United States Patent [19]

Hayashi et al.

[11] Patent Number: 5,014,708
[45] Date of Patent: May 14, 1991

[54] RADIOACTIVE RAY DETECTING THERAPEUTIC APPARATUS

[75] Inventors: Masaaki Hayashi; Koichiro Ishihara; Yutaka Ohshima; Yutaka Yanagawa; Motoyuki Tagawa; Shuichi Takayama; Takashi Tsukaya; Makoto Inaba, all of Hachioji; Toshihiko Hashiguchi, Sagamihara; Hiroki Hibino, Hachioji; Hiroyuki Sasa, Tokyo, all of Japan

[73] Assignee: Olympus Optical Co., Tokyo, Japan

[21] Appl. No.: 290,947

[22] Filed: Dec. 28, 1988

[30] Foreign Application Priority Data

Sep. 14, 1988 [JP] Japan ................. 63-231886

[51] Int. Cl.⁵ .................. A61B 1/00; A61B 10/00; A61B 6/12
[52] U.S. Cl. .................. 128/653 R; 128/4; 128/659; 128/660.03; 604/22; 606/46
[58] Field of Search ........... 128/4, 653 R, 654, 656, 128/657, 658, 659, 660.03, 662.06, 305; 604/22; 606/46, 47

[56] References Cited

U.S. PATENT DOCUMENTS

| | | |
|---|---|---|
| 3,665,916 | 5/1972 | Kobayashi et al. |
| 4,015,592 | 4/1977 | Bradley-Moore ............ 128/659 |
| 4,595,014 | 7/1986 | Barrett et al. ................ 128/654 |
| 4,750,488 | 6/1988 | Wuchinich et al. ........... 604/22 |

FOREIGN PATENT DOCUMENTS

| | | |
|---|---|---|
| 45-40518 | 12/1970 | Japan . |
| 47-5168 | 2/1972 | Japan . |
| 48-4526 | 2/1973 | Japan . |

Primary Examiner—Max Hindenburg
Assistant Examiner—Krista M. Pfaffle
Attorney, Agent, or Firm—Armstrong, Nikaido, Marmelstein, Kubovcik & Murray

[57] ABSTRACT

The radioactive ray detecting therapeutic apparatus of the present invention has an insertable part to be inserted toward an affected part. A therapeutic apparatus for treating the affected part, and a radioactive ray detecting apparatus for detecting radioactive rays discharged out of the affected part and providing signals by which to direct the therapeutic apparatus to the affected part, are provided in the tip part of the insertable part.

29 Claims, 13 Drawing Sheets

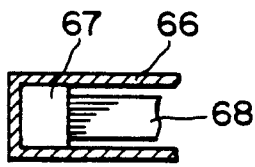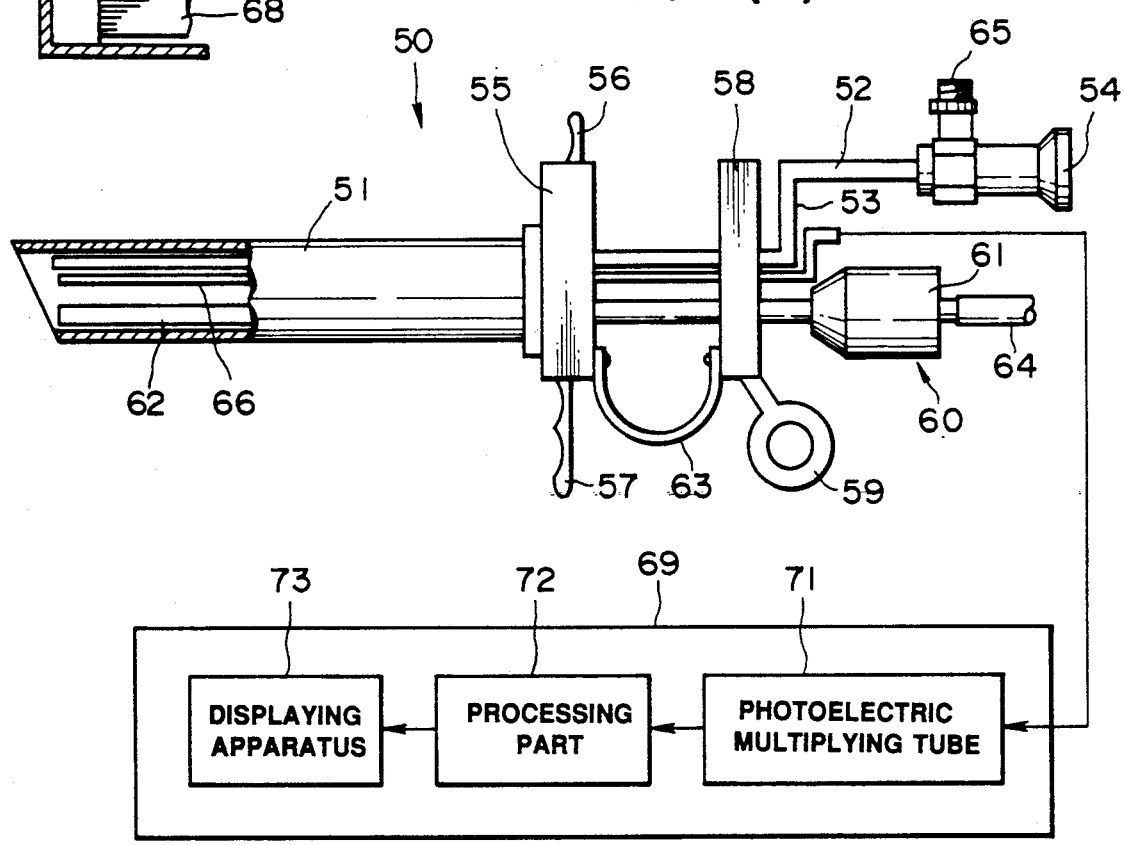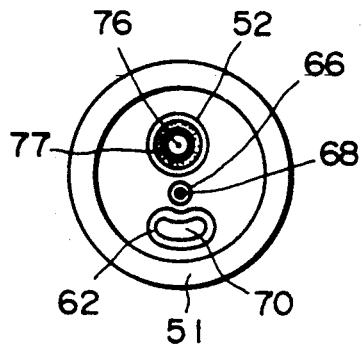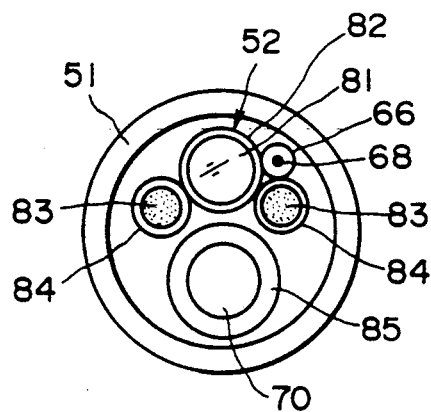

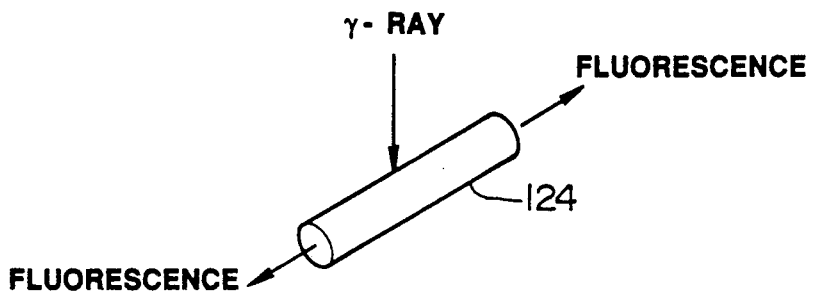
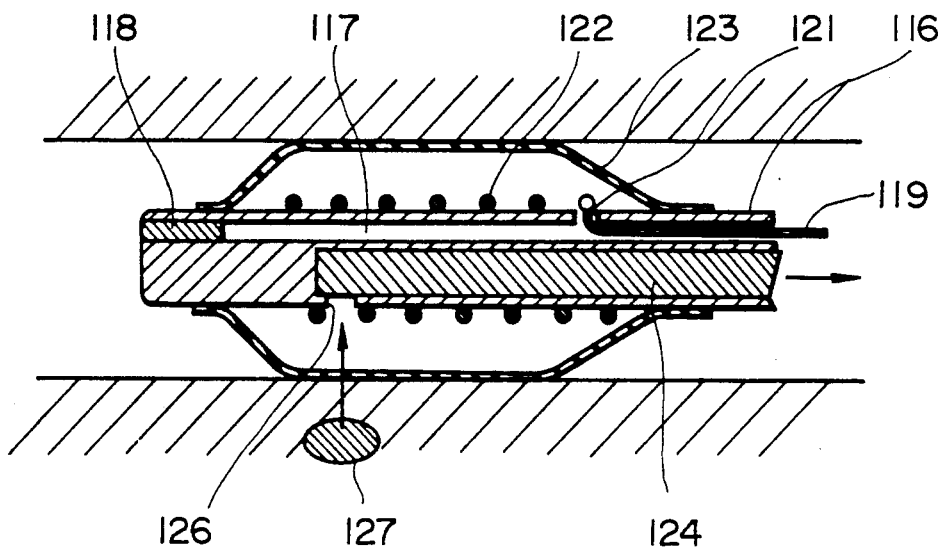
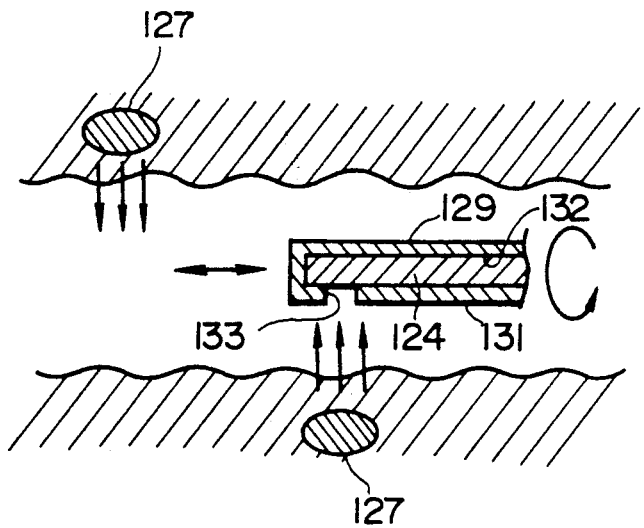

5,014,708

RADIOACTIVE RAY DETECTING THERAPEUTIC APPARATUS

FIELD AND BACKGROUND OF THE INVENTION

This invention relates to a radioactive ray detecting therapeutic apparatus to be inserted into a body cavity.

It is well known that generally cancer cells are so much weaker against heat than normal cells that, when warmed to a temperature near 40° C., they will die.

It is also known that there is a medicine or substance which peculiarly concentrates in cancer cells.

Therefore, as a means of treating a cancer or the like formed within such body cavity as a bladder, there has been already carried out a cauterizing therapy wherein a radioactive substance is injected into a human body to mark cancer cells, radioactive rays discharged out of the cancer cells are detected and the vicinity of the part affected by the cancer is cauterized to be treated.

There has been also carried out a therapy wherein cancer cells are crushed and resected with an ultrasonic treating tool.

As techniques for detecting radioactive rays, there are disclosed publications of Japanese utility model application publication No. 5168/1972, Japanese patent application publication No. 40518/1970 and U.S. Pat. No. 3665916. In the publication of Japanese utility model application publication No. 5168/1972, there is disclosed a technique wherein a sensor for detecting such radioactive rays as $\beta$ rays is introduced into a body cavity through an endoscope to detect and diagnose the presence of a cancer. Also, in the publication of Japanese patent application publication No. 40518/1970, there is shown a technique wherein a light emitting source is provided adjacently to a radioactive ray detecting sensor which can be led into a body through an endoscope and can detect an abnormality of a part and the position of the detecting sensor can be known by the light coming through the living body tissues from this light emitting source. Further, in the publication of Japanese utility model application publication No. 4526/1973 and U.S. Pat. No. 3665916, there is shown a technique wherein a fixing needle is provided on a holder holding a radioactive ray detecting sensor or on the detecting surface of the detecting sensor and the detecting sensor is fixed in a fixed position by driving this fixing needle into tissues.

However, in the above mentioned prior arts, as the radioactive ray detecting apparatus for detecting the affected part discharging radioactive rays and the diagnosing therapeutic apparatus for diagnosing and treating the affected part are separate from each other, first the radioactive ray detecting apparatus is inserted into the body cavity to detect the position of a cancer, a visibly discernible index is attached to the position, then the diagnosing therapeutic apparatus is inserted into the body cavity, the therapy must be made by confirming the index, the diagnosing therapeutic time will become long and pain will be caused to the patient.

Also, there has been a problem that, as the therapy can not be made while detecting the affected part, if the index is missed, no correct diagnosing therapy will be able to be made.

OBJECT AND SUMMARY OF THE INVENTION

An object of the present invention is to provide a radioactive ray detecting therapeutic apparatus whereby, without the need of attaching a visibly discernible index to an affected part discharging radioactive rays, the affected part discharging radioactive rays is detected and therapeutically diagnosed.

Further, an object of the present invention is to provide a radioactive ray detecting therapeutic apparatus whereby an affected part discharging radioactive rays can be quickly therapeutically treated.

A radioactive ray detecting therapeutic apparatus of the present invention comprises a therapeutic means to be inserted into a body cavity to treat an affected part and a radioactive ray detecting means for detecting radioactive rays discharged out of the affected part to be treating by the therapeutic means, the radioactive ray detecting means detects the position of the affected part by measuring the radioactive rays discharged out of the affected part and the detected affected part is treating by the diagnosing therapeutic means.

BRIEF DESCRIPTION OF THE DRAWINGS

FIG. 4 is an explanatory view of the formation of a radioactive ray detecting therapeutic apparatus.

FIG. 5 is an explanatory view of the formation of using a high frequency sucking apparatus and a radioactive ray detecting device as combined.

FIG. 6 is an explanatory view of the formation of a radioactive ray detecting device having a directivity in one direction.

FIG. 7 is an explanatory view of the formation of a radioactive ray detecting apparatus having a directivity in one direction.

FIG. 8 is an explanatory view of the formation of a radioactive ray detecting device having a directivity in four directions.

FIGS. 9 and 10 relate to the fifth embodiment of the present invention.

FIG. 9 (a) is an explanatory view of the entirety of an ultrasonic sucking apparatus.

FIG. 9 (b) is an explanatory view of the tip part of a radioactive ray detecting pipe.

FIG. 10 (a) is an elevation of a sheath interior.

FIG. 10 (b) is of a modification of the formation of a sheath interior.

FIG. 11 (a) is a sectioned view of the tip part of an ultrasonic probe.

FIG. 11 (b) is a sectioned view in the direction A—A' in FIG. 11 (a).

FIG. 12 (a) is a sectioned view of the tip part of an ultrasonic probe.

FIG. 12 (b) is a sectioned view in the direction B—B' in FIG. 12 (a).

FIG. 13 is a sectioned view for explaining the formation of an ultrasonic treating tool.

FIG. 14 (a) is an explanatory view of a jig supporting a probe.

FIG. 14 (b) is an explanatory view of another jig.

FIG. 15 is an explanatory view of a fiber protecting pipe.

FIG. 16 is an explanatory view of a jig having a blade part.

FIG. 17 (a) is an explanatory view of a fiber protecting pipe having a wedge-like tip part.

FIG. 17 (b) is an explanatory view of a fiber protecting pipe having a conical tip part.

FIGS. 18 to 21 relate to the ninth embodiment of the present invention.

FIG. 18 is an explanatory view showing the formation of the tip part of a warming therapeutic treating tool.

FIG. 19 is a perspective view of a warming therapeutic treating tool.

FIG. 20 is an explanatory view of a scintillating plastic optical fiber.

FIG. 21 is an explanatory view showing a warming therapeutic treating tool as being used.

FIG. 22 shows a modification of the ninth embodiment and is an explanatory view of the tip part of a cancer detecting probe.

FIG. 26 is an explanatory view of the formation of a treating part.

FIG. 27 is an explanatory view of the entirety of a radioactive ray detecting treating tool.

FIG. 28 is an explanatory view of a radioactive ray detecting treating tool as being used.

FIG. 29 is an explanatory view showing a radioactive ray detecting sensor as fitted.

FIG. 30 is an explanatory view showing a radioactive ray detecting sensor as fitted in another way.

FIG. 33 is an explanatory view of the formation of the tip part of a radioactive ray detecting treating tool.

FIG. 34 is an explanatory view of a radioactive ray detecting treating tool as being used.

DETAILED DESCRIPTION OF THE PREFERRED EMBODIMENTS OF THE INVENTION

The embodiments of the present invention shall be concretely explained in the following with reference to the drawings.

Figure 1:
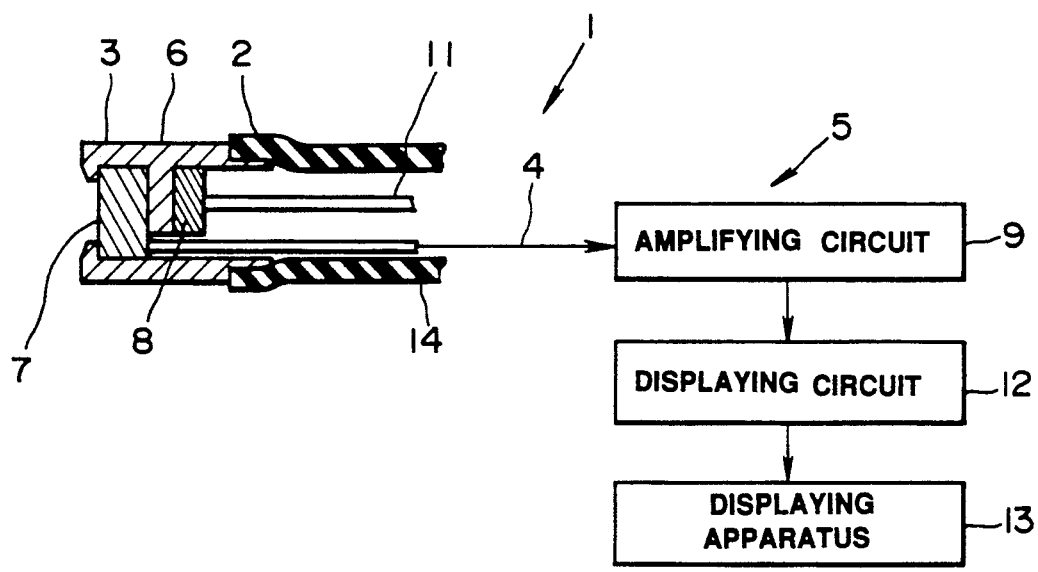
FIG. 1 relates to the first embodiment of the present invention and is an explanatory view of the formation of a radioactive ray detecting therapeutic apparatus.

FIG. 1 relates to the first embodiment of the present invention and is an explanatory view of the formation of a radioactive ray detecting therapeutic apparatus.

In this embodiment, the present invention is applied to a catheter-shaped radioactive ray detecting therapeutic apparatus.

A catheter-shaped radioactive ray detecting therapeutic apparatus 1 of this embodiment comprises an elongate tubular flexible insertable part 2, a tip part 3 connected to the tip of this insertable part 2 and a measuring part 5 connected to a signal wire 4 extended from the rear part of the above mentioned insertable part 2.

The above mentioned tip part 3 is provided with a tip part body 6 formed of a radioactive ray attenuating material having an effect of attenuating radioactive rays. Such radioactive ray detecting device 7 as, for example, a silicon p-n junction device as a radioactive ray detecting means, is provided within this tip part body 6.

The radioactive ray attenuating material to be used for the above mentioned tip part body 6 is a material for weakening the intensity of radioactive rays and is, for example, lead, tungsten, stainless steel, lead glass (plastic or epoxy resin with lead mixed in at a high ratio), concrete, steel (the older, the better) or mercury.

Such heat generating device 8 as, for example, a Zener diode as a diagnosing therapeutic means is provided in the rear of the above mentioned radioactive ray detecting device 7. A signal wire 11 leading to a current source circuit not illustrated is connected to the rear end surface of this heat generating device 8.

A flexible tube member 14 forming the insertable part 2 is externally fitted to the above mentioned tip part body 6 at the rear end.

The above mentioned radioactive ray detecting device 7 is connected through the above mentioned signal wire 4 to an amplifying circuit 9 forming the above mentioned measuring part 5. This amplifying circuit 9 amplifies the signal output from the radioactive ray detecting device 7 and outputs it to a displaying circuit 12. This displaying circuit 12 outputs to a displaying apparatus 13 the signal measuring the detected output and displaying the amount of radioactive rays. The displaying apparatus 13 displays the measured results.

The operation of the radioactive ray detecting therapeutic apparatus 1 formed as in the above shall be explained.

In the case of cauterizing therapy, at a predetermined time before the inspection, a cancer resistor marked with a radioisotope or dioxiglucose likely to concentrate on a cancer (high in activity) is injected into the body by a venous injection or the like. Such reagent concentrates on .the cancer and radioactive rays are discharged out of this cancer.

Then, a catheter-like radioactive ray detecting therapeutic apparatus 1 is inserted into the body cavity, for example, through a treating tool channel of the endoscope. While observing the object image, the tip part body 6 is brought or contacted close to the inspected part to measure the radioactive rays. As cancer cells concentrate radioactive substances, the part strongly radiating radioactive rays is found to be a cancer. The tip part body 6 is closely contacted to this part radiating radioactive rays, that is, the cancer and an electric power is fed to the heat generating device 8 from a current source circuit not illustrated. The heat generating device 8 thereby generates heat and the heat produced by this heat generation is transmitted to the cancer through the tip part body 6 to cauterize the cancer. The cancer dies with this cauterization. Further, the radioactive rays on this periphery are measured and the part in which the radioactive rays are detected is cauterized and treated.

As the radioactive ray detecting therapeutic apparatus 1 of this embodiment has the radioactive ray detecting device 7 which can detect a cancer and the heat generating device 8 which can cauterize the cancer, without taking the conventional operating steps of attaching an index which can discern the affected part and then inserting the cauterizing apparatus into the body to cauterize the affected part, while finding out the affected part with the radioactive ray detection, the affected part can be cauterized with the heat generating device 8. Therefore, the time required for the therapy can be reduced and the therapy can made quickly.

Further, as the radioactive ray detection and cauterization can be made simultaneously, the cancer can be positively cauterized.

Figure 2:
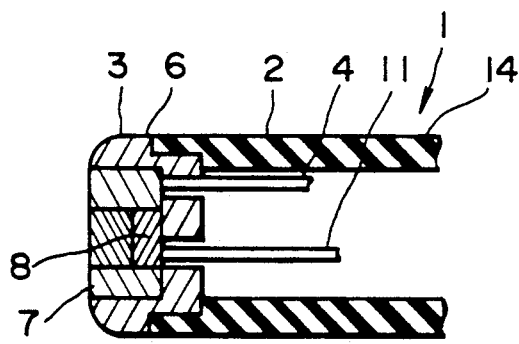
FIG. 2 relates to the second embodiment of the present invention and is an explanatory view of the formation of a radioactive ray detecting therapeutic apparatus.

FIG. 2 relates to the second embodiment of the present invention and is an explanatory view of the formation of a radioactive ray detecting therapeutic apparatus.

A tip part body 6 provided at the tip of an insertable part 2 is provided with such annular radioactive ray detecting device 7 as, for example, a silicon p-n junction device as a radioactive ray detecting means. This radioactive ray detecting device 7 is provided on the inner periphery with such heat generating device 8 as, for example, a Zener diode as a diagnosing therapeutic means and is sealed with a member having high heat conductivity.

The other formations, operations and effects are the same as in the first embodiment.

Figure 3:
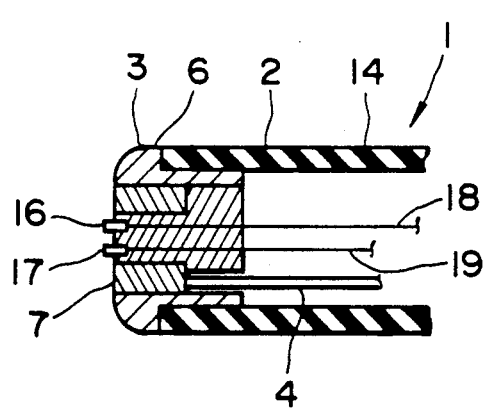
FIG. 3 relates to the third embodiment of the present invention and is an explanatory view of the formation of a radioactive ray detecting therapeutic apparatus.

FIG. 3 relates to the third embodiment of the present invention and is an explanatory view of the formation of a radioactive ray detecting therapeutic apparatus.

A tip part body 6 provided at the tip of an insertable part 2 is provided with such annular radioactive ray detecting device 7 as, for example, a silicon p-n junction device as a radioactive ray detecting means. This radioactive ray detecting device 7 is provided on the inner periphery with bipolar electrodes 16 and 17 as a diagnosing therapeutic means so as to project forward. These bipolar electrodes 16 and 17 are electrically connected to a high frequency current source not illustrated through signal lines 18 and 19 inserted through the insertable part 2.

In such formation as is mentioned above, a high frequency cauterization can be made by flowing a high frequency current between the bipolar electrodes 16 and 17.

Not only the bipolar electrodes 16 and 17 but also a monopolar electrode may be used.

The other formations, operations and effects are the same as in the first embodiment.

Figure 4:
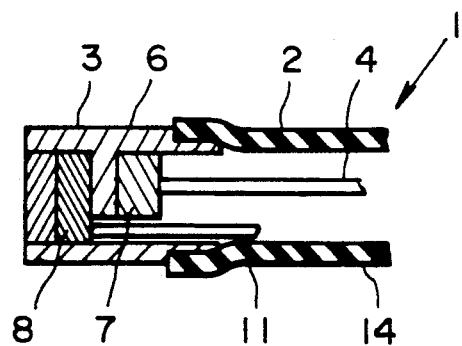
FIGS. 4 to 8 relate to the fourth embodiment of the present invention.
Figure 5:
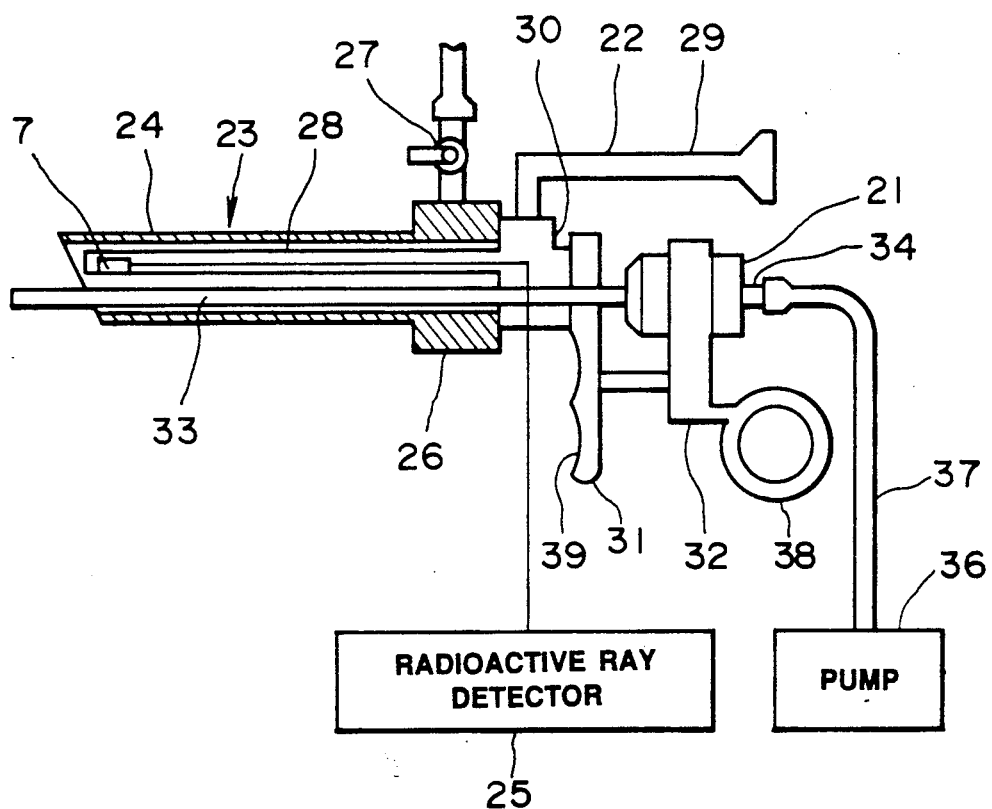
Figure 6:
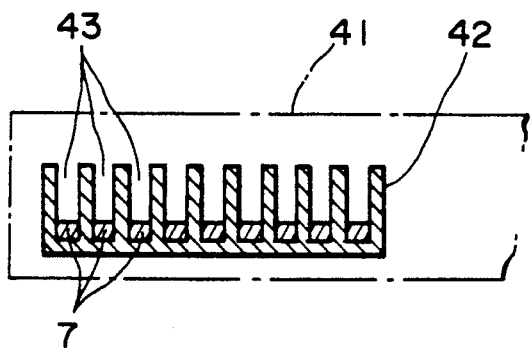
Figure 7:
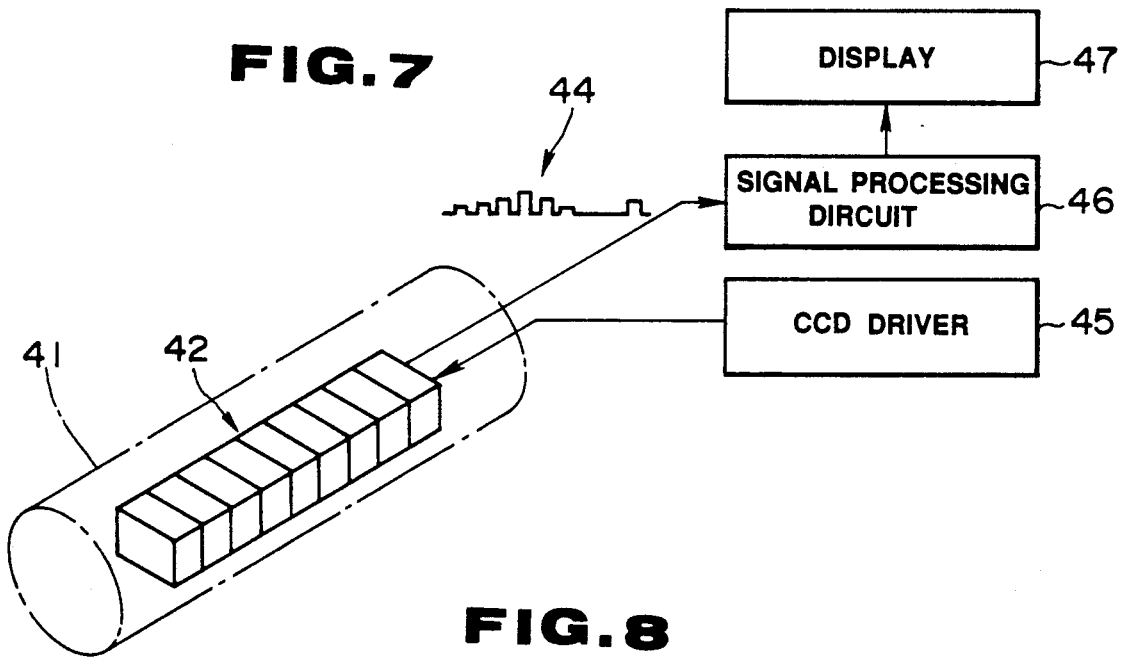
Figure 8:
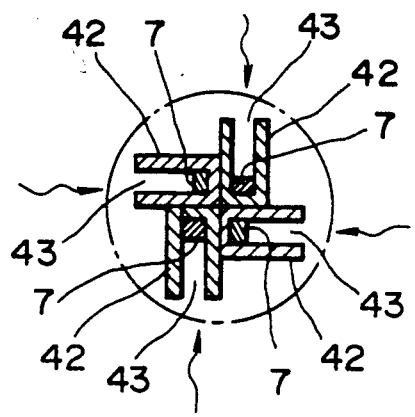

FIGS. 4 to 8 relate to the fourth embodiment of the present invention. FIG. 4 is an explanatory view of the formation of a radioactive ray detecting device combined with a heat generating therapeutic apparatus. FIG. 5 is an explanatory view of the formation in case an ultrasonic sucking therapeutic apparatus and radioactive ray detecting device are used as combined. FIGS. 6-8 show details of the radioactive ray detecting device. FIG. 6 is an explanatory view of the formation of a radioactive ray detecting device having a directivity in one direction. FIG. 7 is an explanatory view of the formation of a radioactive ray detecting apparatus having a directivity in one direction. FIG. 8 is an explanatory view of the formation of a radioactive ray detecting device having directivities in four directions.

The above mentioned tip part 3, as shown in FIG. 4, is provided with a rigid tip part body 6 within which such heat generating device 8 as, for example, a Zener diode as a cauterizing means is provided. A radioactive ray detecting device 7 such as a silicon p-n junction device is provided as a radioactive ray detecting means in the rear of this heat generating device 8.

The other formations, operations and effects are the same as in the first embodiment.

Now, in another arrangement shown in FIG. 5, the affected part can be sucked by using an ultrasonic sucking apparatus 21 and a telescope 22 provided in the tip part with a radioactive ray detecting device 7.

A sheath 23 is provided with an elongate tubular sheath body 24 and a connecting part 26 provided in the rear end part of this sheath body 24. The connecting part is provided with a water feeding cock 27 which can feed an irrigating liquid into the body cavity through the sheath body 24.

A scope inserting part 28 of the telescope 22 is inserted through the above mentioned connecting part 26 from the rear. Such radioactive ray detecting device 7 as, for example, a silicon p-n junction device is provided in the front end part of this scope inserting part 28 and is connected to a radioactive ray detector 25.

A scope connecting part 30 is connected to the rear part of the above mentioned scope inserting part 28. This scope connecting part 30 is provided on the side with an eyepiece part 29. A handle 31 is connected to the scope connecting part 30 at the rear end. A slider 32 fixed with the ultrasonic sucking apparatus 21 is provided in the rear of this handle 31. An elongate tubular vibration transmitting member 33 provided in front of this ultrasonic sucking apparatus 21 is passed through the handle 31 and scope connecting part 30 and is inserted through the sheath body 24 to lead to the tip part of the sheath body 24. The tube path within this vibration transmitting member 33 communicates with a mouthpiece 34 provided at the rear end of the ultrasonic sucking apparatus 21. The irrigating liquid fed into the body cavity from the above mentioned water feeding cock 27 can be sucked by connecting this mouthpiece 34 with a pump 36 through a tube 37.

The above mentioned slider 32 is provided with a finger hanging ring 38 and, by gripping this finger hanging ring 38 and a finger hanging part 39 provided on the handle 31, the vibration transmitting member 33 can be projected at the tip out of the tip part of the sheath body 24 and can be contacted with the affected part to destroy it with the vibration.

Thus, by using both of the radioactive ray detecting device 7 and ultrasonic sucking apparatus 21 as combined, while measuring whether cancer tissues have been positively sucked or not, the treatment can be made and therefore a positive judgment not depending on only the sight is possible.

As in FIGS. 6 and 7, the directivity may be had in the detecting direction of the radioactive ray detecting device 7 shown in FIG. 4 or FIG. 5.

A collimator 42 provided with a plurality of radioactive ray detecting devices 7 is provided within a tubular catheter 41, is formed of a radioactive ray attenuating material having an effect of attenuating radioactive rays and has apertures 43 arranged in a row. The above mentioned radioactive ray detecting devices 7 are provided respectively in the inner parts of these apertures 43.

By enlarging the distance from this aperture 43 to the radioactive ray detecting device 7, the angle of incidence of the radioactive rays on the radioactive ray detecting device 7 can be made smaller and the directivity can be had in the radioactive ray detecting direction.

The apertures 43 open in the direction intersecting at right angles with the lengthwise direction of the catheter 41 so that the radioactive rays incident from a lateral direction may be detected.

The radioactive ray detecting devices 7 which the radioactive rays have entered are respectively read out by a CCD driver 5 and an output signal 44 is delivered to a signal processing circuit 46. The longitudinal distribution and amount for the insertable part of the radioactive rays of the affected part are measured from the signals of the respective radioactive ray detecting devices 7 in the signal processing circuit 46 and are displayed by a display 47.

Also, as in FIG. 8, the apertures 43 of the collimater 42 may be arranged as directed in the directions respectively intersecting at right angles with each other within the catheter 41 so that the radioactive ray distribution radially around the catheter 41 may be three-dimensionally metered.

The other formations, operations and effects are the same as in the first embodiment.

FIGS. 9 and 10 relate to the fifth embodiment of the present invention. FIG. 9 (a) is an explanatory view of the entirety of an ultrasonic sucking apparatus. FIG. 9 (b) is an explanatory view of the tip part of a radioactive ray detecting pipe. FIG. 10 (a) is an elevation of a sheath interior. FIG. 10 (b) is of a modification of the formation of a sheath interior.

In this embodiment, the present invention is applied to an ultrasonic sucking apparatus.

In FIG. 9 (a), an ultrasonic sucking apparatus 50 as a therapeutic means is provided with a cylindrical sheath 51 through which an optical sighting tube 52 is inserted. This optical sighting tube 52 has a rising part 53 in the intermediate part and an eyepiece part 54 at the base end and is substantially crank-like as a whole. A light guide mouthpiece 65 is provided in front of the eyepiece part 54 and is fed with an illuminating light by connecting a light guide cable not illustrated.

As in FIG. 10 (a), a relay lens system 76 is inserted in the lengthwise direction through the center within the optical sighting tube 52 so as to transmit an object image to the eyepiece part 54. A light guide 77 is provided around this relay lens system 76 to transmit to the object the illuminating light fed from the above mentioned light guide mouthpiece 65. The rising part 53 of the optical sighting tube 52 is supported in the front part by a supporting member 55 provided in the base end part of the above mentioned sheath 51.

The above mentioned supporting member 55 is provided with an upper finger hanging part 56 and lower finger hanging part 57. A slider 58 is slidably provided on the part projecting rearward from the above mentioned supporting member 55. This slider 58 is provided with a rear finger hanging part 59 projecting downward and is provided integrally with an ultrasonic treating tool 60. This ultrasonic treating tool 60 is formed of an ultrasonic vibrator 61 and a vibration transmitting member 62 made of metal pipe connected to this ultrasonic vibrator 61 and thereby ultrasonically vibrated and is provided with the vibration transmitting member 62 as slidably inserted through a fitting hole not illustrated formed in the above mentioned supporting member 55. Therefore, the ultrasonic treating tool 60 and the above mentioned slider 58 can be integrally slid in the advancing direction.

A plate spring 63 curved substantially like U is provided between the above mentioned supporting member 55 and slider 58. Against the returning force of this plate spring 63, the above mentioned slider 58 is slid to project the tip part of the vibration transmitting member 62 out of the sheath 51.

The above mentioned ultrasonic vibrator 61 is connected on the rear end surface with one end part of a sucking tube 64 communicating with a sucking path 70 provided within the above mentioned vibration transmitting member 62 and sucking resected tissues. The other end part of this sucking tube 64 is connected to a sucking pump not illustrated.

In FIG. 10 (a), the cross-sectional shape of the above mentioned vibration transmitting member 62 is an ellipse having a concave curved major diameter at its upper side. A radioactive ray detecting pipe 66 is inserted through between the curved concave part of this vibration transmitting member 62 and the above mentioned optical sighting tube 52, is fixed in the rear part in the above mentioned supporting member 55 and is positioned in the front end part near the front end part of the optical sighting tube 52. As in FIG. 9 (b), a scintillator 67 as a radioactive ray detecting means is provided in the tip part within this radioactive ray detecting pipe 66 and is of a single crystal of NaI Tl ) or CsI Tl ) to generate a fluorescence when radioactive rays are incident. The entrance end surface of a light detecting fiber 68 for transmitting the generated fluorescence is provided on the rear end surface of this scintillator 67. This detecting fiber 68 is extended out of the rear end part of the pipe 66 and is connected to a photoelectronic multiplying tube 71 within the radioactive ray detecting apparatus 69. This photoelectronic multiplying tube 71 is connected to a processing part 72 including a multiplying circuit and counting circuit. This processing part 72 displays the measured results in a displaying apparatus 73.

The operation of the ultrasonic sucking apparatus 50 formed as mentioned above shall be explained.

At a predetermined time before making an inspection, such compound having a property of peculiarly concentrating in cancer tissues as a monochronal resistor and an RI (radioactive isotope) are combined with each other and are injected into the body. After the RI concentrates in cancer tissues, the optical sighting tube 52, radioactive ray detecting pipe 66 and vibration transmitting member 62 are inserted through the sheath 51 driven into the body.

If cancer tissues are positioned in front of the radioactive ray detecting pipe 66, the radioactive rays discharged out of the cancer tissues will enter the scitillator 67 provided in the tip part of the pipe 66. When the radioactive rays enter the scintillator 67, a fluorescence will be generated. The fluorescence is led to the photoelectronic multiplying tube 71 by the detecting fiber 68 and is amplified and photoelectrically converted. The electric signal obtained by this photoelectric conversion is output to the processing part 72 and in this processing part is further amplified, has the light amount counted and outputs a signal adapted to such displaying apparatus 73 as, for example, a digital counter. The operator recognizes by the displaying apparatus 73 that cancer tissues are present in front of the radioactive ray detecting pipe 66, grips the fingers hung on the finger hanging parts 56, 57 and 59, projects the tip part of the vibration transmitting member 62 out of the sheath 51 and pushes it against the cancer tissues. Thereafter, when an electric current is passed through the ultrasonic vibrator 61 by a current source not illustrated, the vibration transmitting member 62 will be ultrasonically vibrated by the ultrasonic waves generated by this ultrasonic vibrator 61 and the cancer tissues will be resected. The resected cancer tissues are sucked into a sucking apparatus not illustrated by the sucking tube 64 through the sucking path 70 formed within the vibration transmitting member 62. The resection is made until the radioactive rays are no longer detected by the radioactive ray detecting apparatus 69.

As mentioned above, in this embodiment, while detecting radioactive rays, the resection is made and therefore even cancer tissues hard to observe with a naked eye can be resected without leaving them.

Further, as the scintillator 67 for detecting radioactive rays is provided near the tip part of the vibration transmitting member 62 for the resection, the radioactive ray detected part, that is, the cancer tissues can be positively resected.

As the scintillator 67 is provided also near the tip part of the optical sighting tube 52, the radioactive ray detected part and the observed part can be made to correspond to each other.

The sheath interior 51 may be formed as in FIG. 10 (b).

A glass tube 82 forming an optical sighting tube 52 and provided with a relay lens system 81 is inserted through the upper part within the sheath 51. This relay lens system 81 transmits the object image which can be observed with a naked eye from the eyepiece part 54. A pair of light guide tubes 84 through which light guides 83 are respectively inserted are inserted on both sides below this glass tube 82 so that the illuminating light fed from the light guide mouthpiece 65 may be transmitted to the observed part.

A radioactive ray detecting pipe 66 is inserted through the space enclosed with the above mentioned glass tube 82, light guide tube 84 and the inner wall of the sheath 51. A scintillator 67 as a radioactive ray detecting means is provided at the tip of this radioactive ray detecting pipe 66.

A vibration transmitting member 85 forming an ultrasonic treating tool 60 and having a circular cross-sectioned shape is inserted below the above mentioned glass tube 82 and light guide tubes 84 within the sheath 51.

As the radioactive ray detecting pipe 66 is thus arranged among the glass tube 82, light guide tube 84 and sheath inner wall, the space within the sheath 51 can be effectively utilized.

Figures 11A, 11B:
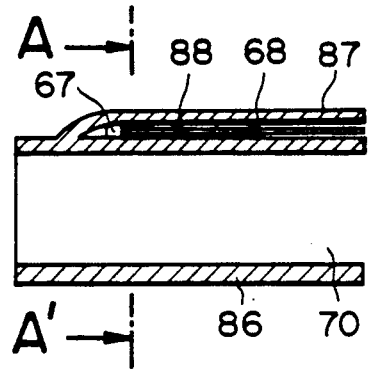
FIG. 11 relates to the sixth embodiment of the present invention.

FIG. 11 relates to the sixth embodiment of the present invention. FIG. 11 (a) is a sectioned view of the tip part of a vibration transmitting member. FIG. 11 (b) is a sectioned view in the direction A—A' in FIG. 11 (a).

In this embodiment, the vibration transmitting member of the ultrasonic sucking apparatus described in the fifth embodiment is provided with a scintillator.

A vibration transmitting member 86 provided in front of the ultrasonic vibrator 61 and transmitting an ultrasonic vibration to resect cancer tissues has a substantially circular cross-sectioned shape. A projection 87 is provided in the lengthwise direction on a part of the outer peripheral wall of this vibration transmitting member 86. A fiber inserting path 88 through which a radioactive ray detecting fiber 68 is inserted is provided within this projection 87. This projection 87 is provided to the vicinity of the tip part of the vibration transmitting member 86 which is formed to be circular on the outer peripheral wall in the tip part. The fiber inserting path 88 is provided also to the tip part of the projection 87. A scintillator 67 as a radioactive ray detecting means is provided in this tip part. The incident end surface of the above mentioned detecting fiber 68 is provided on the rear end surface of this scintillator 67. This fiber 68 is connected to the radioactive ray detecting apparatus described in the fourth embodiment and can detect radioactive rays.

In this embodiment, as the scintillator 67 is provided within the vibration transmitting member 86 for resection, radioactive rays can be detected in a position nearer to the resected part.

The other formations, operations and effects are the same as in the fifth embodiment.

Figures 12A, 12B:
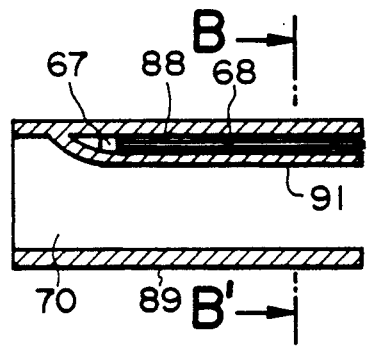
FIG. 12 relates to the seventh embodiment of the present invention.

FIG. 12 relates to the seventh embodiment of the present invention. FIG. 12 (a) is a sectioned view of the tip part of a vibration transmitting member. FIG. 12 (b) is a sectioned view in the direction B—B' in FIG. 12 (a).

In this embodiment, the projection in the sixth embodiment is provided on the inner peripheral wall of a vibration transmitting member.

A vibration transmitting member 89 provided in front of an ultrasonic vibrator 61 and transmitting an ultrasonic vibration to resect cancer tissues has a substantially circular cross-sectioned shape. A projection 91 is provided in the lengthwise direction on a part of the inner peripheral wall of this vibration transmitting member 89. A fiber inserting path 88 through which a radioactive ray detecting fiber 68 is inserted is provided within this projection 91. This projection 91 is provided to the vicinity of the tip part of the vibration transmitting member 89 and the inner peripheral wall of the tip part of the vibration transmitting member 89 is formed to be circular. The fiber inserting path 88 is provided also to the tip part of the projection. A scintillator 67 as a radioactive ray detecting means is provided in this tip part. The incident end surface of the above mentioned detecting fiber 68 is provided on the rear end surface of this scintillator 67. This fiber 68 is connected to the radioactive ray detecting apparatus described in the fourth embodiment and can detect radioactive rays.

In this embodiment, as the scintillator 67 is provided within the vibration transmitting member 89 for the same resection as in the sixth embodiment, radioactive rays can be detected in a position nearer to the resected part.

The other formations, operations and effects are the same as in the fifth embodiment.

Figure 13:
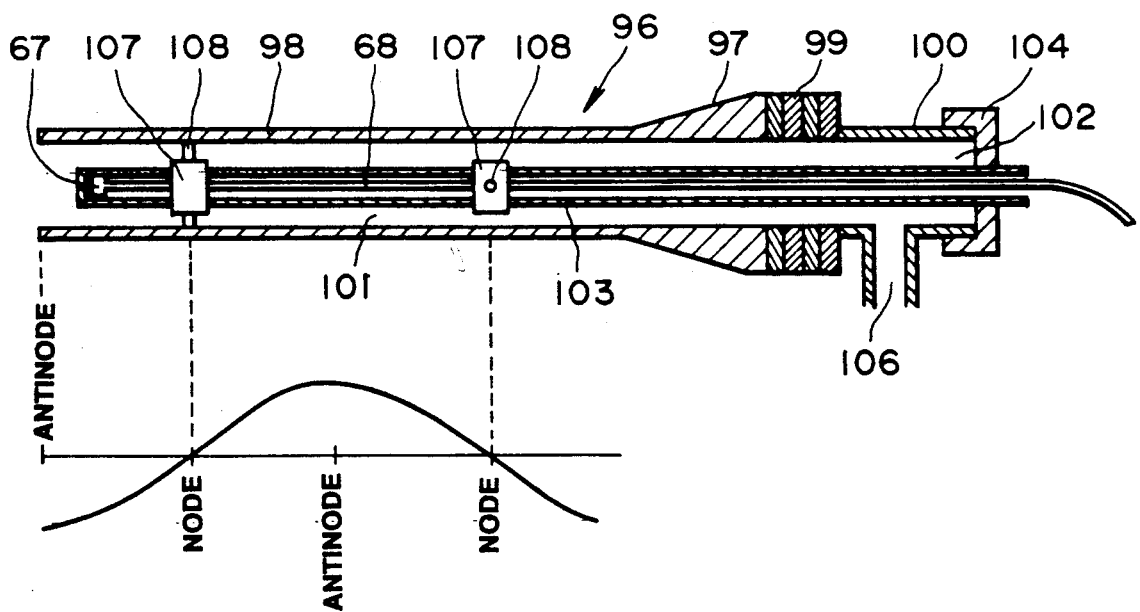
FIGS. 13 to 17 relate to the eighth embodiment of the present invention.

FIGS. 13 to 17 relate to the eighth embodiment of the present invention. FIG. 13 is a sectioned view for explaining the formation of an ultrasonic treating tool.

Figure 14A:
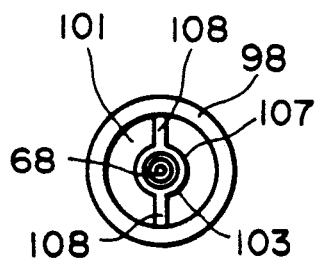
Figure 14B:
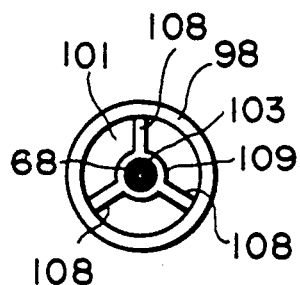
Figure 15:
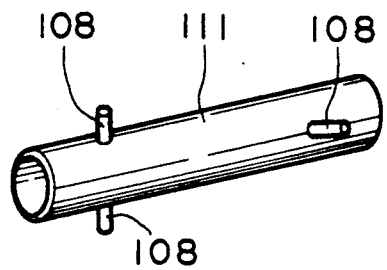
Figure 16:
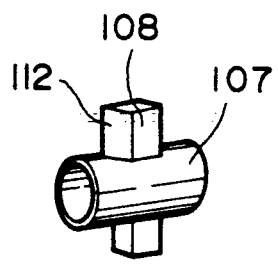
Figure 17A:
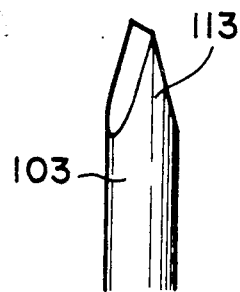
Figure 17B:
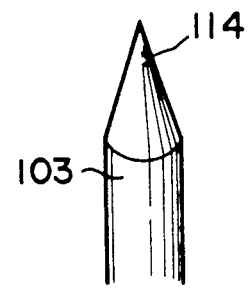

FIG. 14 (a) is an explanatory view of a jig supporting a vibration transmitting member. FIG. 14 (b) is an explanatory view of another jig. FIG. 15 is an explanatory view of a fiber protecting pipe. FIG. 16 is an explanatory view of a jig having a blade part. FIG. 17 (a) is an explanatory view of a fiber protecting pipe having a wedge-like tip part. FIG. 17 (b) is an explanatory view of a fiber protecting pipe having a conical tip part.

In this embodiment, a radioactive ray detecting fiber is concentrically provided within a vibration transmitting member.

In FIG. 13, an ultrasonic treating tool 97 forming an ultrasonic sucking apparatus 96 as a therapeutic means is provided with an ultrasonic vibrator 99 and a vibration transmitting member 98 as an ultrasonic wave transmitter connected to the front part of this ultrasonic vibrator 99 and made of an ultrasonically vibrated metal pipe. A connecting part 100 is connected to the rear end of this ultrasonic vibrator 99. An inserting hole 102 is provided on the rear end surface of this connecting part 100 and communicates within the ultrasonic vibrator 99 with a sucking path 101 provided within the vibration transmitting member 98 and sucking resected tissues. A drain port 106 draining the sucked tissues out of the above mentioned sucking path 101 is provided on the side of the connecting part 100. Within the above mentioned sucking path 101, the fiber protecting pipe 103 inserted through the inserting hole 102 is supported by a jig 107 so as to be positioned in the center in the lengthwise direction of the, vibration transmitting member 98.

The inserting hole 102 is sealed with such plug member 104 as, for example, of rubber.

A radioactive ray detecting fiber 68 is inserted through the above mentioned fiber protecting pipe 103 and its front end surface is in contact with the rear end surface of the scintillator 67 as a radioactive ray detecting means provided within the front end part of the pipe 103 so as to be able to transmit the fluorescence generated by the scintillator 67. This detecting fiber 68 is connected at the rear end to the radioactive ray detecting apparatus described in the fifth embodiment.

The above mentioned jig 107 is formed to be cylindrical as in FIGS. 14 (a) and is externally fitted to the fiber protecting pipe 103. Further, on the outer peripheral surface of this jig 107, two supporting arms 108 project in the diametral direction so that the angles formed with each other may be equal. In order to be prevented from being broken by the friction, in the position to be a node in case the vibration transmitting member 98 ultrasonically vibrates, this supporting arm 108 will contact the inner peripheral wall of the vibration transmitting member 98 to hold the fiber protecting pipe 103. In FIG. 13, two jigs 107 are provided and the supporting arms 108 of the respective jigs 107 are so arranged as to have an angle of about 90 degrees with each other.

As in FIG. 14 (b), a jig 109 provided with three supporting arms 108 so that the angles formed with one another may be equal may be arranged in the position to be a node of the vibration.

Also, instead of using the separate fiber protecting pipe 103 and jig 107 as combined, as shown in FIG. 15, the supporting arms 108 may project in the diametral direction out of the outer peripheral wall of the fiber protecting pipe 111. In this case, too, when the fiber protecting pipe 111 is inserted into the vibration transmitting member 98, the supporting arm 108 will contact the position to be a node of the vibration.

Further, as in FIG. 16, the supporting arm 108 projected out of the fiber protecting pipe 111 or jig 107 or 109 is provided with a blade part 112 so that the tissues sucked into the sucking path 101 may be finely broken by the blade part 112 and may be prevented from clogging the sucking path 101.

Further, as in FIG. 17, in the tip part of the fiber protecting pipe 103, so that the tissues may be easily sucked as in FIG. 17 (a), a wedge-like tip part 113 may be formed and, as in FIG. 17 (b), a conical tip part 114 may be formed.

As the scintillator 67 as a radioactive ray detecting means is provided in the center of the vibration transmitting member 98 as mentioned above, the radioactive ray emitting source, that is, the cancer tissues can be more precisely resected.

The other formations, operations and effects are the same as in the fifth embodiment.

Figure 18:
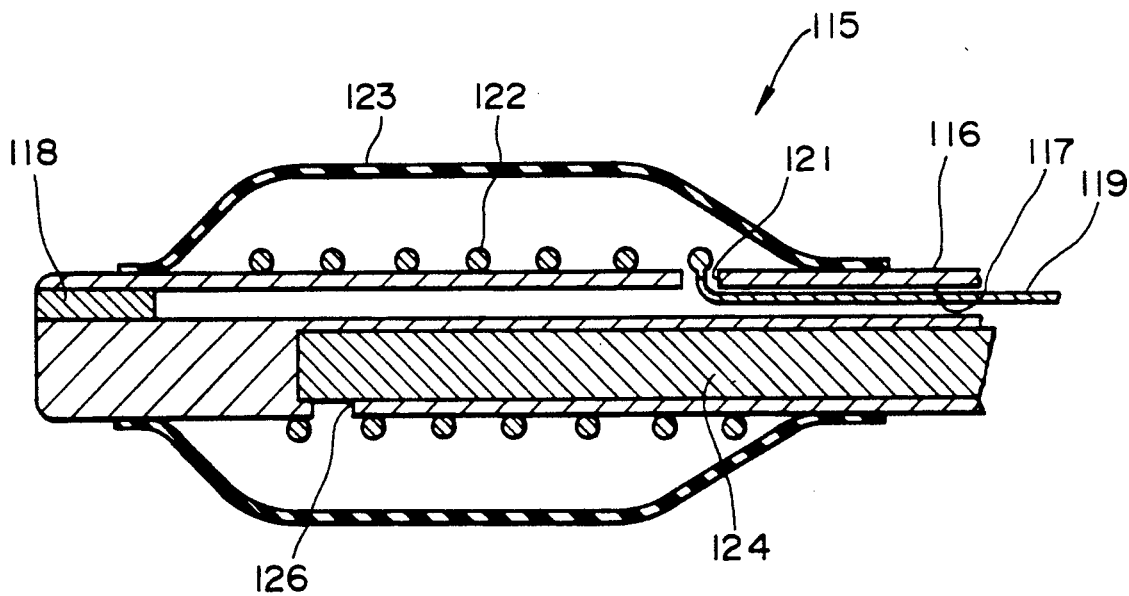
Figure 19:
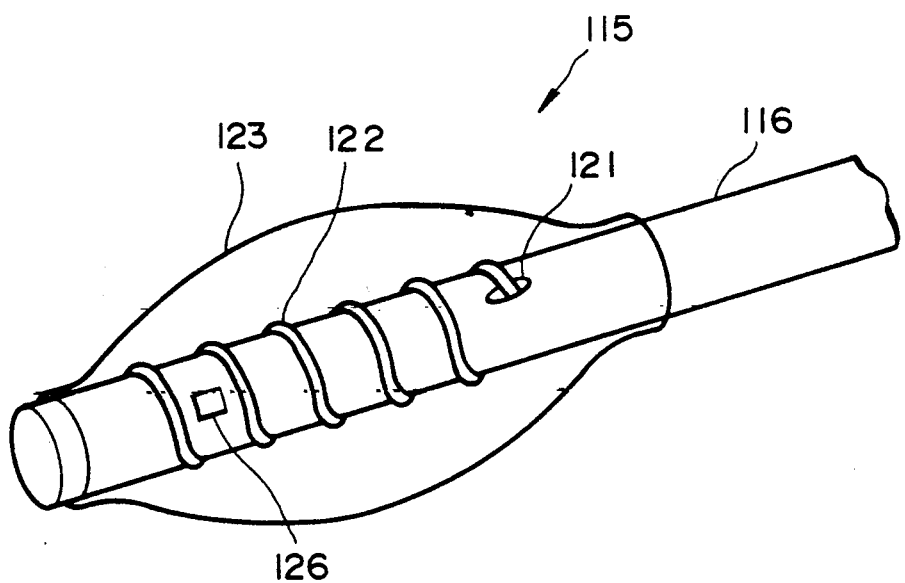

FIGS. 18 to 21 relate to the ninth embodiment of the present invention. FIG. 18 is an explanatory view showing the formation of the tip part of a warming therapeutic treating tool. FIG. 19 is a perspective view of a warming therapeutic treating tool. FIG. 20 is an explanatory view of a scintillating plastic optical fiber. FIG. 21 is an explanatory view showing a warming therapeutic treating tool as being used.

In this embodiment, as shown in FIG. 20, a scintillating plastic optical fiber 124 as a radioactive ray detecting means emitting a fluorescence from the center axial direction when $\gamma$ rays are applied from the side is used for a warming therapeutic treating tool.

In FIG. 18, a warming treating tool 115 as a therapeutic means inserted through a treating tool channel of an endoscope has an elongate porous tube 116 formed of a radioactive ray attenuating material effective to attenuate radioactive rays. An electric cable path 117 communicating with the tip part is provided within this porous tube 116 and is closed in the tip part of the porous tube 116 with a sealing member 118. An electric cable 119 is inserted through the electric cable path 117, is exposed outward of the porous tube 116 through a communicating hole 121 provided in the outer peripheral wall near the tip part of the porous tube 116 and is connected to one end of an RF electrode 122 formed to be coil-like as a therapeutic means spirally wound on the outer peripheral wall of the porous tube 116 on the tip side from the communicating hole 121. The RF electrode 122 is connected at the other end with an electric cable not illustrated. This electric cable 119 and the electric cable not illustrated are inserted through the electric cable path 117, are extended rearward of the porous tube 116 and are connected to a high frequency current source not illustrated. Also, for example, an air feeding apparatus not illustrated is connected to the rear of the above mentioned electric cable path 117.

An expansible balloon 123 is provided in the tip part of the above mentioned porous tube 116 so as to cover the RF electrode 122 and is inflated with air fed from the above mentioned air feeding apparatus not illustrated and passed through the electric cable path 117 and communicating hole 121.

The above mentioned scintillating plastic optical fiber (which shall be abbreviated as SPOF hereinafter) 124 is inserted through the above mentioned porous tube 116 and is arranged to lead to the tip part of the porous tube 116. A detecting window 126 is provided in the part covered by the above mentioned balloon 123 on the outer peripheral wall of the porous tube 116 through which this SPOF 124 is inserted. The SPOF 124 is exposed on the outer periphery from this detecting window 126 and is connected to a radioactive ray detecting apparatus not illustrated in the rear end part of the porous tube 116.

The operation of the warming therapeutic treating tool 115 formed as mentioned above shall be explained.

The porous tube 116 through which the treating tool channel and others of the endoscope are inserted is projected in the tip part provided with the, balloon 123 out of the tip part of the endoscope. When the porous tube 116 is to be inserted through the treating tool channel, the balloon 123 will not be fed with air and will be kept contracted.

In FIG. 21, the same as in the first embodiment, a cancer resistor marked with a radioisotope or dioxiglucose is administered to the patient in advance and radioactive rays are discharged from a cancer 127. When the porous tube 116 reaches the vicinity of the cancer 127 and the cancer 127 is positioned on the side of the detecting window 126, the radioactive rays will pass through the detecting window 126 and will reach the SPOF 124. As explained in FIG. 20, when the radioactive rays are incident from the side, the SPOF 124 will generate a fluorescence in the center axial direction. This fluorescence is transmitted through the SPOF 124 and reaches a radioactive ray detecting apparatus not illustrated. In this radioactive ray detecting apparatus, the radioactive ray intensity is calculated from the fluorescence and is displayed or an alarm is sounded. The inspector knows the presence of the cancer 127 by such display or alarm, operates an air feeding apparatus not illustrated and feeds air into the balloon 123 through the electric cable path 117 to inflate the balloon 123. Then, an electric current is passed through the RF electrode 122 through the electric cable 119 from a high frequency current source not illustrated to make the RF electrode 122 generate heat. The heat is transmitted to the balloon 123 in contact with the affected part to make a warming therapy.

Now, in the conventional therapeutic method, prior to the therapy, the position of the affected part has been confirmed with an endoscope or radioactive ray detecting apparatus and, then, the therapy has been made with a warming therapeutic treating tool. However, in this embodiment, as the warming therapeutic treating tool 115 has the SPOF which can detect radioactive rays, the radioactive ray detection and warming therapy can be simultaneously made and the therapeutic time can be made short. The warming therapy can be made by making the RF electrode 122, positively correspond to the cancer.

A scintillating crystal or a semiconductor detector may be used instead of the SPOF.

FIG. 22 shows a modification of the ninth embodiment and is an explanatory view of the tip part of a cancer detecting probe.

A cancer detecting probe 129 is provided with a tubular member 131 formed of a material effective to attenuate radioactive rays. A tube path 132 closed in the front end part is provided within this tubular member 131. The SPOF 124 described in the ninth embodiment is inserted through this tube path 132. A detecting window 133 detecting radioactive rays is provided on the front peripheral wall of the tubular member 131 so that the radioactive rays having passed through this detecting window 133 may reach the SPOF.

In detecting the cancer 127 with the cancer detecting probe 129 formed as mentioned above, the detecting window 133 is positioned on the side of the position in which the cancer 127 is thought to be present. The SPOF 124 is enclosed on the periphery with a radioactive ray attenuating material, therefore has a directivity in the radioactive ray detecting direction and detects only the radioactive rays entering from the side of the detecting window 133. Therefore, the probe 129 is moved forward and rearward in the lengthwise direction and is rotated with respect to the center axis to be able to detect the range of the cancer 127.

Figure 23:
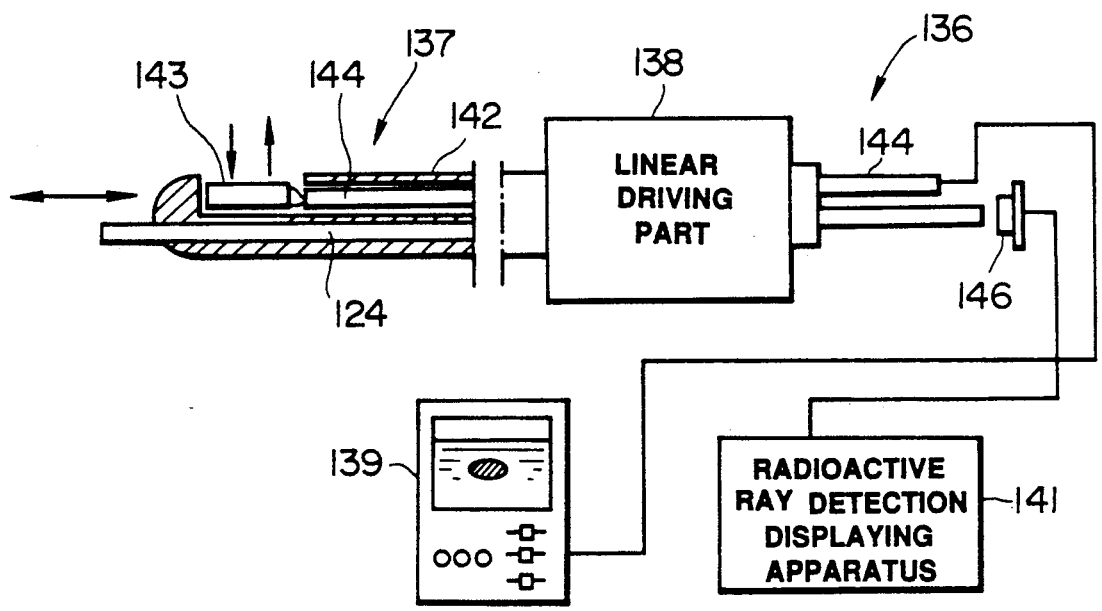
FIG. 23 relates to the tenth embodiment of the present invention and is an explanatory view showing the formation of the entirety of a linear type extremely fine ultrasonic probe having a radioactive ray detecting function.

FIG. 23 relates to the tenth embodiment of the present invention and is an explanatory view showing the formation of the entirety of a linear type extremely fine ultrasonic probe having a radioactive ray detecting function.

In this embodiment, a linear type extremely fine ultrasonic probe is applied to the present invention.

A linear type extremely fine ultrasonic probe 136 as a therapeutic means comprises a probe body 137 to be inserted into a body cavity, a linear driving part 138 moving this probe body 137 in the lengthwise direction, an ultrasonic picture image apparatus 139 displaying an ultrasonic picture image and a radioactive ray detecting and displaying apparatus 141 for detecting radioactive rays.

The above mentioned probe body 137 is provided with a porous tube 142 formed of a material effective to attenuate radioactive rays. A lead wire 144 electrically connected to an ultrasonic device 143 provided in the tip part and receiving and transmitting ultrasonic waves is inserted through this porous tube 142 and further the SPOF 124 as a means for detecting radioactive rays described in the ninth embodiment is longitudinally movably inserted through the porous tube 142. The porous tube 142 is provided in the rear part with the above mentioned linear driving part 138 so that, in inspecting the affected part, the porous tube 142 may be moved in the lengthwise direction. Also, the linear driving part 138 can transmit and indication of the displacement of the porous tube 142 to the above mentioned ultrasonic picture image apparatus 139 and radioactive ray detecting and displaying apparatus 141.

The above mentioned lead wire 144 is extended from the rear end part of the porous tube 142 and is electrically connected to the above mentioned ultrasonic picture image apparatus 139 to provide picture image data. The ultrasonic picture image apparatus 139 produces an ultrasonic cross-sectioned image from the picture image data and the displacement transmitted from the above mentioned linear driving part 138 and displays it.

The rear end surface of the above mentioned SPOF 124 is extended out of the rear part of the porous tube 142 and faces a photodiode 146 so that the fluorescence generated by the SPOF 124 may enter the photodiode 146 which is electrically connected to the above mentioned radioactive ray detecting and displaying apparatus 141 to deliver radioactive ray data converted to an electric signal by the photodiode 146.

The operation of the linear type extremely fine ultrasonic probe formed as mentioned above shall be explained.

The SPOF is slightly projected out of the tip part of the porous tube 142 inserted into the fine tube cavity. Radioactive rays are discharged out of such radioactive ray source as iodine accumulated in advance through a monochronal resistor or the like from an ulcer. These radioactive rays enter the SPOF 124 from the side and make the SPOF 124 generate a fluorescence which is transmitted through the SPOF 124 and enters the photodiode 146. The photodiode 146 electrically converts the fluorescence and delivers radioactive ray data to the radioactive ray detecting and displaying apparatus 141.

At the same time, the ultrasonic device 143 transmits ultrasonic waves and receives reflection waves reflected from the affected part. The received signal is delivered as ultrasonic picture image data to the ultrasonic picture image apparatus 139. These ultrasonic picture image data display the ultrasonic cross-sectioned image of the same part as the part detected by radioactive rays with the radioactive ray detecting and displaying apparatus 141 by adding the displacement transmitted from the linear driving part.

According to this embodiment, the part opposed in the lengthwise direction of the probe 137 can be diagnosed.

Also, as the intensity of radioactive rays can be detected in addition to the ultrasonic cross-sectioned image of the diagnosed part, the presence of an ulcer can be positively known and the precision of the ultrasonic cross-sectioned image diagnosis can be increased.

Figure 24:
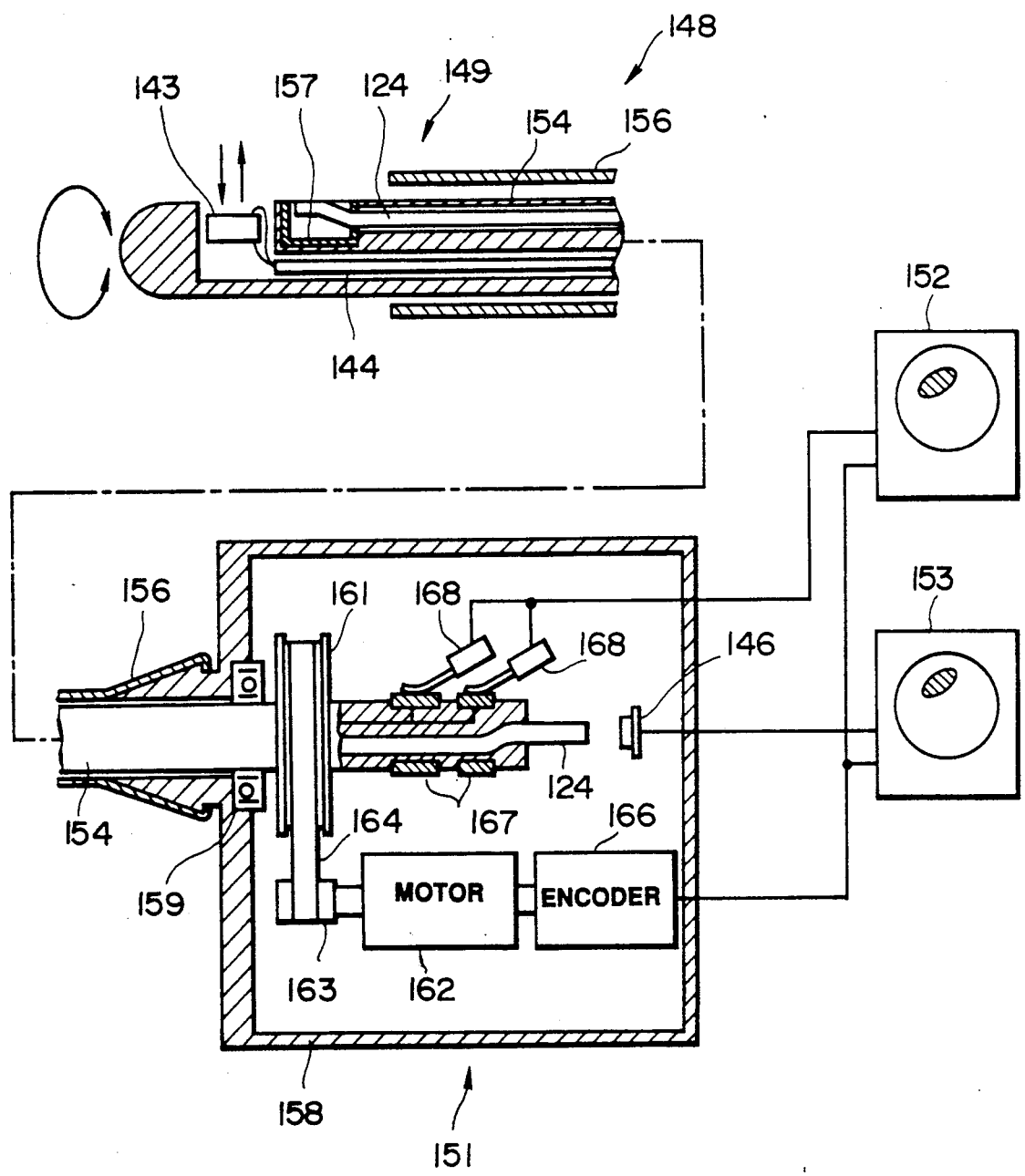
FIG. 24 relates to the 11th embodiment of the present invention and is an explanatory view showing the formation of the entirety of a radial type extremely fine ultrasonic probe.

FIG. 24 relates to the 11th embodiment of the present invention and is an explanatory view showing the formation of the entirety of a radial type extremely fine ultrasonic probe.

In this embodiment, the present invention is applied to a radial type extremely fine ultrasonic probe.

A radial type extremely fine ultrasonic imaging probe 148 as a therapeutic means comprises a probe body 149, a radial driving part 151 for rotating this probe body 149 with respect to the center axis, an ultrasonic picture image apparatus 152 for displaying an ultrasonic picture image and a radioactive ray detecting and displaying apparatus 153 for detecting radioactive rays.

The above mentioned probe body 149 is provided with a porous tube 154 and a sheath 156 for inserting this porous tube 154 and formed of a material effective to attenuate radioactive rays. A lead wire 144 electrically connected to an ultrasonic device 143 provided in the tip part and receiving and transmitting ultrasonic waves sidewise is inserted through this porous tube 154. Further, the SPOF 124 as a radioactive ray detecting means for detecting radioactive rays described in the ninth embodiment is inserted through the porous tube 154. The SPOF 124 at the front end is provided in the rear of the ultrasonic device 143 and is enclosed with a collimator 157 formed of a radioactive ray attenuating material effective to attenuate radioactive rays and opened in the same direction as the signal receiving and transmitting direction of the ultrasonic device 143.

The above mentioned sheath 156 is connected at the rear end to the case 158 of the above mentioned radial driving part 151. The porous tube 154 at the rear end is passed into the case 158 and is rotatably supported by a ball bearing 159 provided in this case. A large pulley 161 is provided on the porous tube 154 in the rear of the ball bearing 159 and has a torque transmitted by a belt 164 from a small pulley 163 provided on the driving shaft of a motor 162 whose rotation center axis is provided in parallel with the center axis of the porous tube 154. An encoder 166 is provided in the rear end part of the motor 162. Signals representing the ultrasonic wave receiving and transmitting direction and radioactive ray detecting direction are delivered to the above mentioned ultrasonic picture image apparatus 152 and radioactive ray detecting apparatus 153 from the rotating position of the motor 162.

Ring-like terminals 167 are externally fitted in the rear of the large pulley 161 to the above mentioned porous tube 154 and are electrically connected with the lead wire extended from the above mentioned ultrasonic device 143. Sliding terminals 168 electrically contact these ring-like terminals 167 so that electric signals may be conducted even in case the ring-like terminals 167 rotate. The sliding terminals 168 deliver the ultrasonic picture image data of the ultrasonic device 143 to the above mentioned ultrasonic picture image apparatus 152.

The SPOF 124 extends out of the rotation center of the rear end surface of the porous tube 154 so that the rear end surface of this SPOF 124 may face a photodiode 146. This photodiode 146 receives the fluorescence generated by the SPOF 124, converts it to an electric signal and delivers it as radioactive ray data to the radioactive ray detecting and displaying apparatus 153.

The operation of the radial type extremely fine ultrasonic imaging probe formed as mentioned above shall be explained.

The probe body 149 is inserted into the fine tube cavity and the ultrasonic apparatus 143 provided in the tip part of the porous tube 154 and the aperture of the collimator 157 are projected out of the tip part of the sheath 156. The porous tube 154 is rotated by the motor 162 through the small pulley 163, belt 164 and large pulley 161 with the lengthwise direction center as a rotary axis. The radioactive rays other than those entering the sidewise aperture are intercepted by the collimator 157. When the porous tube 154 makes one rotation, the SPOF 124 will be able to detect radioactive rays in the diametral direction. As the ultrasonic device 143 has also as a measuring direction the same direction as of the SPOF 124, when the porous tube 154 makes one rotation, the ultrasonic device will be able to measure the same part as the part measured by the porous tube 154. The measuring direction is detected by the encoder 166 provided in the rear end part of the motor 162 and is delivered as position data to the ultrasonic picture image apparatus 152 and radioactive ray detecting and displaying apparatus 153.

When radioactive rays enter the tip part of the SPOF 124 through the aperture of the collimator, the SPOF 124 will generate a fluorescence which is transmitted through the SPOF 124 and enters the photodiode 146. This photodiode 146 electrically converts the fluorescence and delivers it as radioactive ray data to the radioactive ray detecting and displaying apparatus 153. The displaying apparatus 153 operates them together with the position data and displays the radioactive ray intensity with a picture image.

On the other hand, the ultrasonic device 143 transmits ultrasonic waves to the same part as the radioactive ray detecting part, receives the reflected waves and outputs them as ultrasonic picture image data to the ultrasonic picture image apparatus 152 through the ring-like terminals 167 and sliding terminals 168. The ultrasonic picture image apparatus 152 displays an ultrasonic cross-sectioned image from the picture image data and position data.

According to this embodiment, as the radioactive ray detection around the probe 149 and the ultrasonic cross-sectioned image can be simultaneously obtained, a quick diagnosis can be made.

The other formations, operations and effects are the same as in the tenth embodiment.

Figure 25:
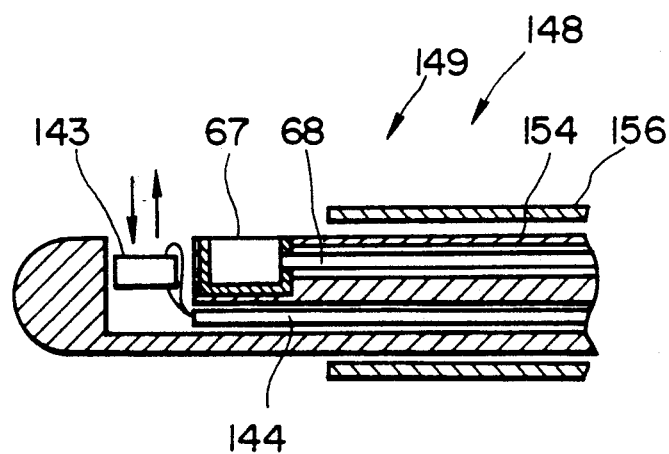
FIG. 25 relates to a modification of the 11th embodiment and is an explanatory view of the formation of the tip part of a probe.

FIG. 25 relates to a modification of the 11th embodiment and is an explanatory view of the formation of a probe tip part.

In this embodiment, the scintillator 67 as a radioactive ray detecting means described in the fifth embodiment is provided within the collimator 157 described in the 11th embodiment. The entrance end surface of a detecting fiber 68 formed of a fiber bundle is provided through the collimator 157 to be in contact with the rear end surface of this scintillator 67. This detecting fiber 68 inserted through the porous tube 154 makes a fluorescence generated by the scintillator 67 enter a photodiode 146

The other formations, operations and effects are the same as in the 11th embodiment.

Figure 26:
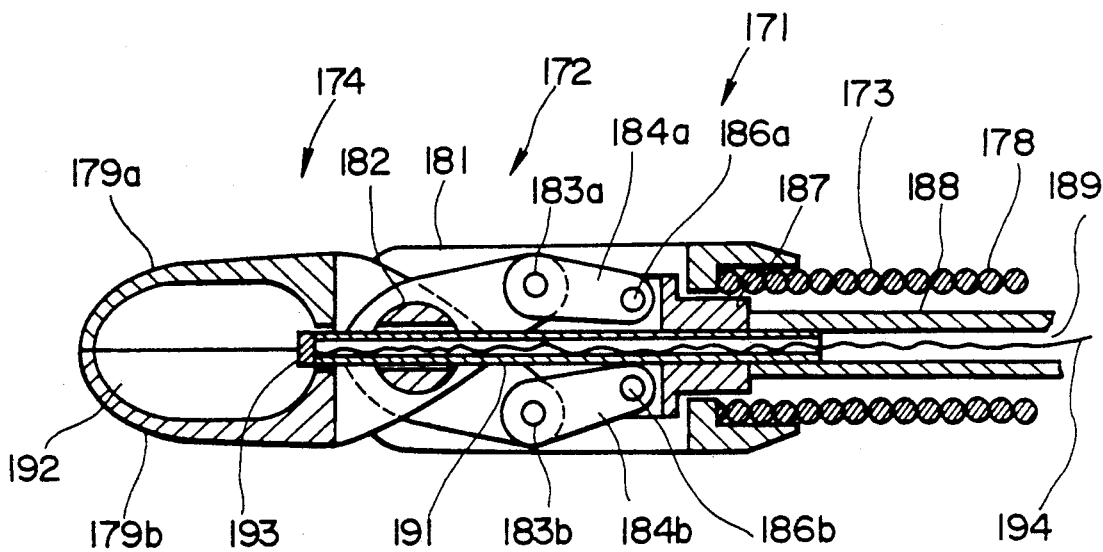
FIGS. 26 to 30 relate to the 12th embodiment of the present invention.
Figure 27:
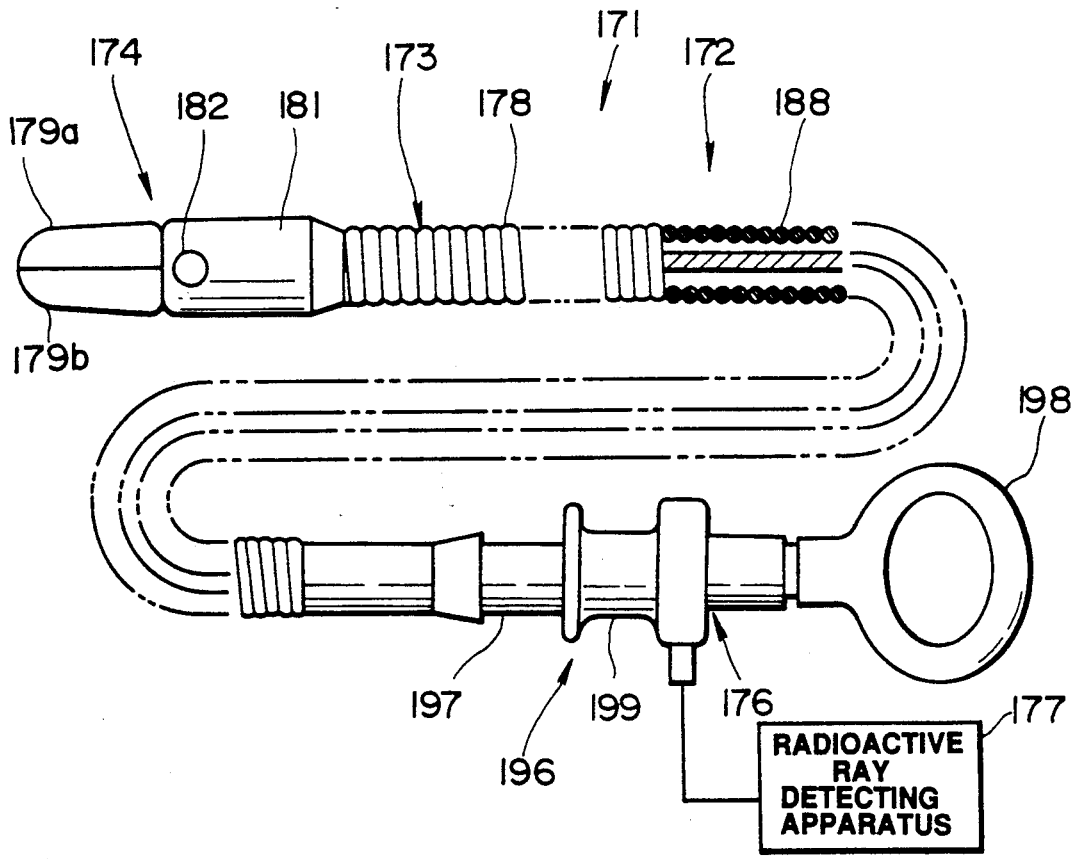
Figure 28:
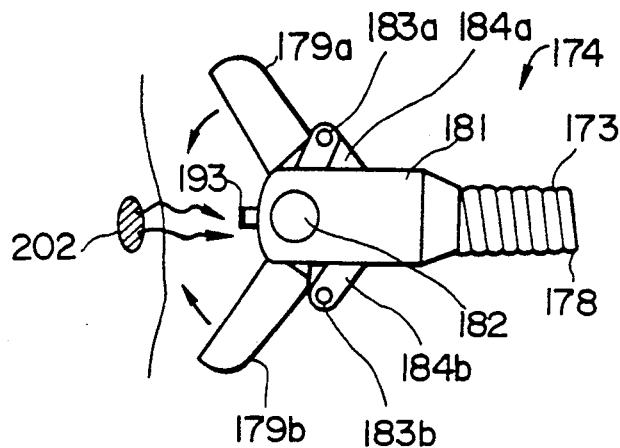
Figure 29:
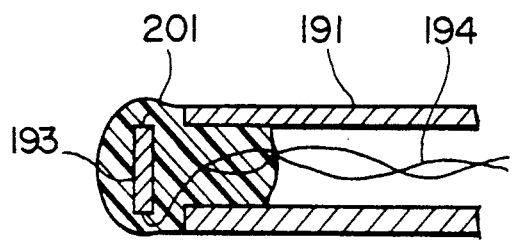
Figure 30:
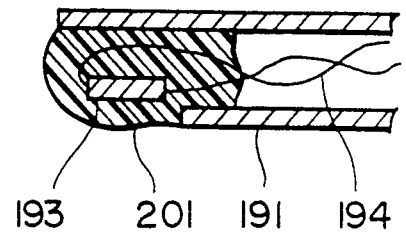

FIGS. 26 to 30 relate to the 12th embodiment of the present invention. FIG. 26 is an explanatory view of the formation of a treating part. FIG. 27 is an explanatory view of the entirety of a radioactive ray detecting treating tool. FIG. 28 is an explanatory view of a radioactive ray detecting treating tool as being used. FIG. 29 is an explanatory view showing a radioactive ray detecting sensor as fitted. FIG. 30 is an explanatory view showing a radioactive ray detecting sensor as fitted in another way.

In this embodiment, the present invention is applied to a biopsic forceps.

In FIG. 27, a biopsic forceps 172 as a therapeutic means forming a radioactive ray detecting treating tool 171 comprises a sheath 173, a treating part 174 provided in the tip part of this sheath 173 and an operating part 176 provided in the base end part of the above mentioned sheath 173. Further, the biopsic forceps 172 is connected to a radioactive ray detecting apparatus 177.

The above mentioned sheath 173 is formed of a closely wound coil 178 made by closely winding a wire made, for example, of a stainless steel. The above mentioned treating part 174 has a pair of cup-like biopsic cups 179a and 179b formed of such radioactive ray attenuating material effective to attenuate radioactive rays as, for example, lead or stainless steel coated on the outer periphery with a resin or the like. These biopsic cups 179a and 179b are pivoted by a pin 182 to a sleeve 181 connected to the tip of the above mentioned sheath 173 so as to be openable on the tip side.

As shown in FIG. 26, the above mentioned biopsic cups 179a and 179b are rotatably fitted in the base end parts to the end parts on one side of link plates 184a and 184b by pins 183a and 183b. These link plates 184a and 184b are rotatably fitted in the end parts on the other side to a connecting member 187 by pins 186a and 186b.

A twisted operating wire 188 is connected at the tip to the above mentioned connecting member 187, is inserted through the above mentioned sheath 173 and is led out to the operating part 176. This operating wire 188 has a hollow part 189. A tubular holding member 191 provided to pass through the above mentioned pin 182 and connecting member 187 is internally fitted to the tip part on the treating part 174 side within this hollow part 189. This holding member 191 is exposed in the tip part within a space part 192 formed by being enclosed in with the above mentioned biopsic cups 179a and 179b. A radioactive ray detecting sensor 193 as a radioactive ray detecting means such as, for example, a silicon p-n junction device which can detect radioactive rays is fitted to the tip part of this exposed holding member 191 shown in FIG. 29, the radioactive ray detecting sensor 193 is sealed on the periphery with a waterproof sealing resin 201. Further, this sealing resin 201 fixes the radioactive ray detecting sensor 193 to the holding member 191. Signal wires 194 are extended out of this radioactive ray sensor 193 and are inserted through the holding member 191 and hollow part 189 to lead to the operating part 176.

As shown in FIG. 30, the holding member 191 may be formed of a radioactive ray attenuating material effective to attenuate radioactive rays and the radioactive ray detecting sensor 193 may be shielded with this holding member 191 partly on the periphery so that the detecting direction of the radioactive ray detecting sensor 193 may be sidewise.

Further, as shown in FIGS. 29 and 30, the formation of sealing the radioactive ray detecting sensor 193 with the sealing resin 201 may be applied to the radioactive ray detecting probe.

In the above mentioned operating part 176, an operating part body 196 is connected to the rear end of the above mentioned sheath 173 and is formed of a shaft part 197 and a finger hanging ring 198 formed in the rear end part of this shaft part 197. A slider 199 is slidably loosely fitted to the above mentioned shaft part 197 and the above mentioned operating wire 188 is connected at the rear end to this slider 199.

The operation of the radioactive ray detecting treating tool 171 formed as in the above shall be explained.

In the case of biopsizing a cancer by using the radioactive ray detecting treating tool 171 of this embodiment, at a predetermined time before the inspection, a cancer resistor marked with a radioisotope or dioxiglucose likely to concentrate on a cancer (which is high in activity) is injected into a body by a venous injection or the like. Such reagent concentrates on a cancer 202 from which radioactive rays, for example, γ rays are discharged.

Then, the biopsic forceps 172 is inserted into the body cavity, for example, through a forceps channel of an endoscope. In the case of inserting it, as the radioactive ray detecting sensor 193 is shielded on the periphery with the biopsic cups 179a and 179b, radioactive rays will not be detected.

After the insertion, the operator hangs the thumb on the finger hanging ring 198, hangs the pointing finger and middle finger of the same hand on the slider 199 and slides the slider 199 forward along the shaft part 197 of the operating part body 196. The slider 199 relaxes the operating wire 188 and opens the biopsic cups 179a and 179b of the treating part 4 through a link mechanism by link plates 184a and 184b. When the biopsic cups 179a and 179b that have shielded radioactive rays are open, γ rays discharged out of the cancer 202 will be detected by the radioactive ray detecting sensor 193. The radioactive ray detecting apparatus 177 electrically connected to the radioactive ray detecting sensor 193 has a measuring means by which the intensity of the radioactive rays can be measured. The treating part 174 is moved around the cancer 202 with the biopsic cups 179a and 179b opened, the part in which the radioactive rays are most intense is detected and the position of the cancer 202 is determined.

After the position of the cancer 202 is discriminated, the slider 199 is moved rearward, the operating wire 188 is pulled to close the biopsic cups 179a and 179b and the cancer 202 is biopsized.

In this embodiment, in case the biopsic cups 179a and 179b are approached to the cancer 202, the part of the cancer 202 will be made hard to sight from the visual field of the endoscope operator, being hidden by the biopsic cups 179a and 179b. However, as the part in which the radioactive rays are most intense is detected, the cancer 202 can be positively biopsized.

The tip parts of the biopsic cups 179a and 179b may be formed of a material which can transmit radioactive rays so that the directivity of the radioactive ray detecting sensor 193 may be made forward and further radioactive rays may be detected while the biopsic cups 179a and 179b are not opened.

Figure 31:
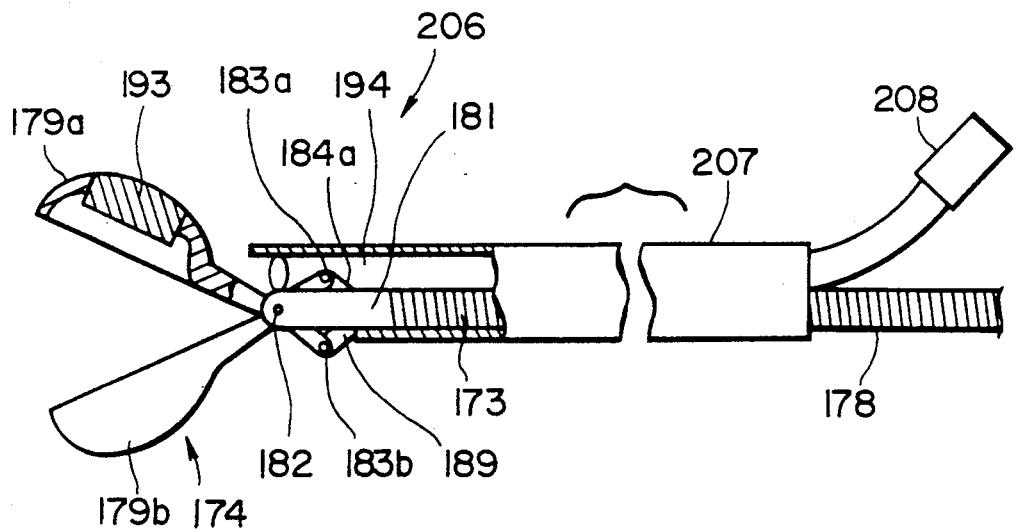
FIG. 31 relates to the 13th embodiment of the present invention and is an explanatory view of the entirety of a radioactive ray detecting treating tool.

FIG. 31 relates to the 13th embodiment of the present invention and is an explanatory view of the entirety of a radioactive ray detecting treating tool.

In this embodiment, the signal wires inserted through the biopsic forceps of the 12th embodiment are set along the sheath.

A sheath 173 forming a biopsic forceps 206 as a diagnosing therapeutic means is inserted through a flexible tube member 207 and is provided in the tip part with biopsic cups 179a and 179b and at the rear end with an operating part 176.

A signal wire 194 connected to a radioactive ray detecting sensor 193 as a radioactive ray detecting means provided in the biopsic cup 179a is inserted through the above mentioned tube member 207 and is provided in the rear end part with a connector 208 so as to be removably connected with a radioactive ray detecting apparatus 177.

The other formations, operations and effects are the same as in the 12th embodiment.

In case the connector part is provided between the radioactive ray detecting sensor 193 and signal wire 194 and radioactive rays are not detected, the signal wire 194 may be removed.

Figure 32:
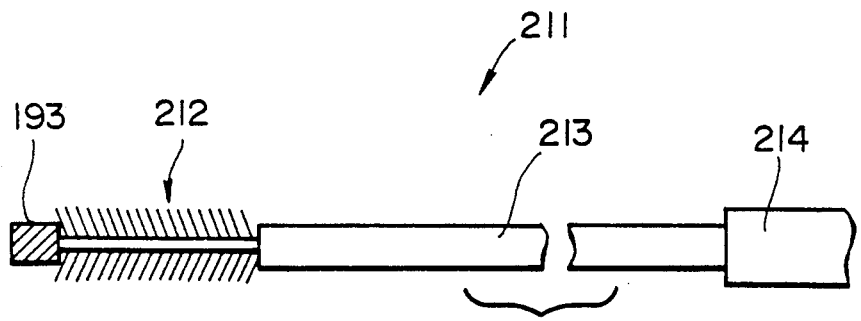
FIG. 32 relates to the 14th embodiment of the present invention and is an explanatory view of the entirety of a radioactive ray detecting treating tool.

FIG. 32 relates to the 14th embodiment of the present invention and is an explanatory view of the entirety of a radioactive ray detecting treating tool.

In this embodiment, a cell diagnosing brush 211 as a diagnosing therapeutic means with which the cells of the affected part can be taken by rubbing the affected part is provided in the tip part with a radioactive ray detecting sensor 193 as a radioactive ray detecting means.

A cell diagnosing brush 211 of this embodiment is provided in the tip part with a radioactive ray detecting sensor 193 and in the rear of this radioactive ray detecting sensor 193 with a brush part 212 as a treating part and is connected in the rear of this brush part 212 with a coaxial wire 213 electrically connected to the above mentioned radioactive ray detecting sensor 193. This coaxial wire 213 is provided at the rear end with a connector 214 so as to be able to be electrically connected to the radioactive ray detecting apparatus 177.

The cell diagnosing brush 211 formed as in the above is inserted into a body cavity, for example, as inserted through a forceps channel of an endoscope. The intensity of radioactive rays is measured by the radioactive ray detecting sensor 193 to detect the position of the cancer 202. After the detection, the coaxial wire 213 is held, pulled and relaxed, the cancer 202 is rubbed with the brush part 212 and cancer cells are taken.

The other formations, operations and effects are the same as in the 12th embodiment.

Figure 33:
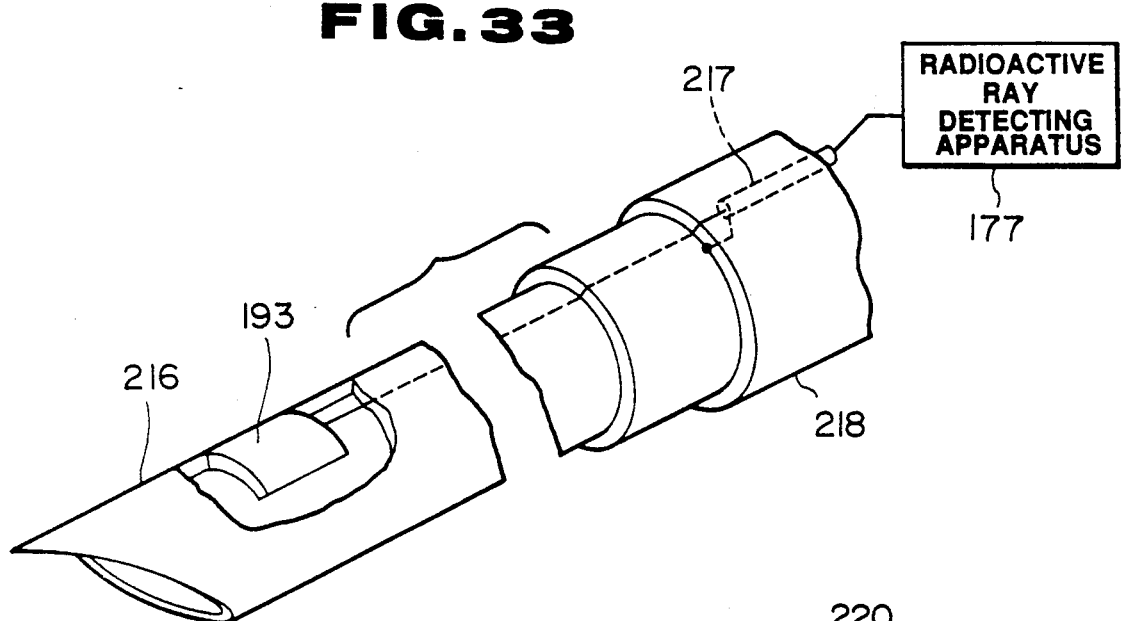
FIGS. 33 and 34 relate to the 15th embodiment of the present invention.
Figure 34:
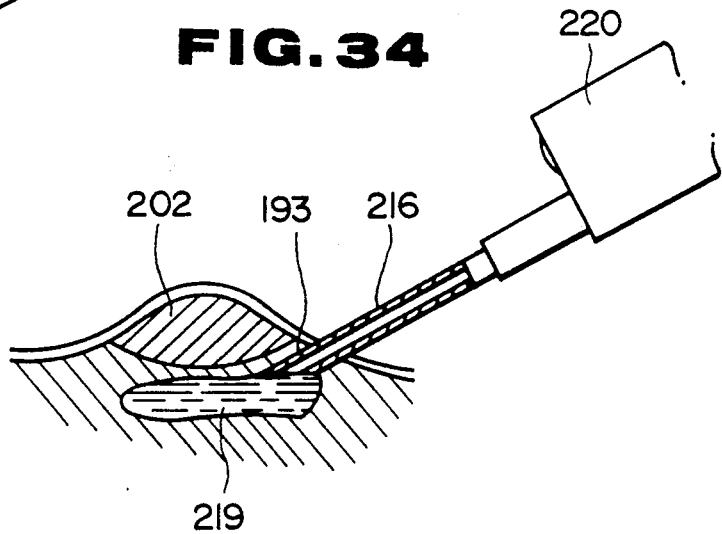

FIGS. 33 and 34 relate to the 15th embodiment of the present invention. FIG. 33 is an explanatory view of the formation of the tip part of a radioactive ray detecting treating tool. FIG. 34 is an explanatory view of a radioactive ray detecting treating tool as being used.

In this embodiment, a radioactive ray detecting sensor 193 is provided in the tip part of an injection needle 216.

The radioactive ray detecting sensor 193 as a radioactive ray detecting means is provided in the tip part of the injection needle 216 as a therapeutic means and is connected to a radioactive ray detecting apparatus 177 through a shielding wire 217. A flexible tube member 218 is connected to the above mentioned injection needle 216 at the rear end so that, for example, a physiological saline 219 may be fed.

The injection needle 216 by the above formation is inserted through a forceps channel and is inserted into a body cavity. The position of a cancer 202 is detected by the radioactive ray detecting sensor 193 and, while seeing with an endoscope, the injection needle 216 is driven into the peripheral part of this cancer 202 while measuring the intensity of the radioactive rays. At the time of starting the drive of the needle, the radioactive rays will become intense. When the tip part, that is, the radioactive ray detecting sensor 193 of the injection needle 216 is driven below the cancer 202, the radioactive rays will become weak. In the position where the radioactive rays become weak, the drive of the injection needle is stopped. Then, for example, the physiological saline 219 is injected through the injection needle 216. The cancer 202 will float up when the physiological saline 219 is injected. The part floating up is caught with a wire and is resected with an electric knife.

According to this embodiment, as a physiological saline can be positively injected below the cancer 202, the cancer can be resected without being left.

The other formations, operations and effects are the same as in the 12th embodiment.

As explained above, according to the present invention, by having both of a radioactive ray detecting means and therapeutic means, without the need of attaching an index which can be discriminated by sight to the affected part, the therapeutic time can be shortened. Further, as the radioactive ray detection and the therapy can be made simultaneously, the cancer will not be missed and can be positively treated.

What is claimed is:

1. A radioactive ray detecting therapeutic apparatus comprising:
   an insertable part to be inserted toward an effected part within a body;
   a therapeutic means provided in a tip part of said insertable part for treating said affected part; and
   a radioactive ray detecting means in said insertable part for detecting radioactive rays discharged out of said affected part and providing signals by which to direct an operator to guide said therapeutic means to said affected part.

2. A radioactive ray detecting therapeutic apparatus comprising:
   an insertable part to be inserted toward an affected part within a body;
   a therapeutic means provided in a tip part of said insertable part for treating said affected part; and
   a radioactive ray detecting means provided in a tip part of said insertable part for detecting radioactive rays discharged out of said affected part and providing signals by which to direct an operator to guide said therapeutic means to said affected part.

3. A radioactive ray detecting therapeutic apparatus according to claim 1 or 2 further comprising a radioactive ray attenuating means for regulating a direction in which the radioactive rays discharged out of said affected part enter said radioactive ray detecting means.

4. A radioactive ray detecting therapeutic apparatus according to claim 3 wherein said radioactive ray attenuating means includes a radioactive ray attenuating member positioned to enclose the periphery of said radioactive ray detecting means except in a predetermined radioactive ray detecting direction.

5. A radioactive ray detecting therapeutic apparatus according to claim 3 wherein said radioactive ray attenuating means comprises a radioactive ray attenuating member having a plurality of apertures opening in radial directions of said insertable part.

6. A radioactive ray detecting therapeutic apparatus according to claim 3 wherein said radioactive ray attenuating means comprises a plurality of radioactive ray attenuating members each member having a plurality of apertures, each of said plurality of apertures opening in a direction substantially at a right angle to the axial direction of said insertable part and said members apertures opening in radial directions intersecting at right angles with directions of the other members.

7. A radioactive ray detecting therapeutic apparatus according to claim 1 or 2 wherein said therapeutic means is a heat generating device for cauterizing said affected part.

8. A radioactive ray detecting therapeutic apparatus according to claim 1 or 2 wherein said therapeutic means is an ultrasonic device for resecting tissue of said affected part by means of ultrasonic vibration and wherein said apparatus further includes sucking means for removing said resected tissue.

9. A radioactive ray detecting therapeutic apparatus according to claim 8 wherein a telescope is provided in said insertable part and said radioactive ray detecting means is provided in a tip part of said telescope.

10. A radioactive ray detecting therapeutic apparatus according to claim 8 further including a radioactive ray detecting pipe, a sheath which forms part of said insertable part, and a telescope, wherein said radioactive detecting means is provided in a tip part of said radioactive ray detecting pipe which is inserted into said sheath together with said telescope, and said therapeutic means includes a vibration transmitting member for resecting tissue of the affected part.

11. A radioactive ray detecting therapeutic apparatus according to claim 8 wherein said ultrasonic device includes a vibration transmitting member and said radioactive ray detecting means is provided in a tip part of said vibration transmitting member.

12. A radioactive ray detecting therapeutic apparatus according to claim 8 wherein said ultrasonic device includes a vibration transmitting member including a sucking path and a fiber protecting pipe, and wherein said radioactive ray detecting means is provided in a tip part of said fiber protecting pipe which is inserted in said insertable part through said sucking path within the vibration transmitting member.

13. A radioactive ray detecting therapeutic apparatus according to claim 12, further including a supporting member, wherein said fiber protecting pipe is supported from the vibration transmitting member by said supporting member at a node of the vibration of said vibration transmitting member when the ultrasonic probe vibrates.

14. A radioactive ray detecting therapeutic apparatus according to claim 1 or 2, further comprising a biopsic forceps for taking samples of tissue cells of said affected part.

15. A radioactive ray detecting therapeutic apparatus according to claim 14 wherein said radioactive ray detecting means is enclosed within biopsic cups of said biopsic forceps comprised of a radioactive ray attenuating material, except while said forceps is taking samples of tissue cells.

16. A radioactive ray detecting therapeutic apparatus according to claim 15 wherein said radioactive ray attenuating member includes any one of the group consisting of lead, tungsten, stainless steel, lead glass, concrete, steel and mercury.

17. A radioactive ray detecting therapeutic apparatus according to claim 1 or 2 wherein said therapeutic means is a warming treating tool for warming and treating said affected part.

18. A radioactive detecting therapeutic apparatus according to claim 17 comprising a balloon in the tip part of the insertable part and further comprising warming electrodes and detecting window through which said radioactive rays enter the radioactive ray detecting means.

19. A radioactive ray detecting therapeutic apparatus according to claim 1 or 2, further comprising an ultrasonic imaging probe for obtaining an ultrasonic picture image within a body.

20. A radioactive ray detecting therapeutic apparatus according to claim 19 further comprising an ultrasonic picture image display means for displaying said ultrasonic picture image of the body in which said radioactive rays are detected by said radioactive ray detecting means.

21. A radioactive ray detecting therapeutic apparatus according to claim 19 wherein said ultrasonic probe is provided with a driving means for moving said insertable part in a axial direction.

22. A radioactive ray detecting therapeutic apparatus according to claim 19 wherein said ultrasonic probe is provided with a driving means for rotating said insertable part about an axis of rotation.

23. A radioactive ray detecting therapeutic apparatus according to claim 1 or 2, further comprising a cell diagnosing brush for taking cells of the affected part.

24. A radioactive ray detecting therapeutic apparatus according to claim 23 wherein said radioactive ray detecting means is provided in a tip part of said cell diagnosing brush.

25. A radioactive ray detecting therapeutic apparatus according to claim 1 or 2 wherein said therapeutic means is an injection needle for administering a medicinal solution to the affected part.

26. A radioactive ray detecting therapeutic apparatus according to claim 25 wherein said radioactive ray detecting means is provided in a tip part of said injection needle.

27. A radioactive ray detecting therapeutic apparatus according to claim 1 or 2 wherein said radioactive ray detecting means is a silicon p-n junction type device.

28. A radioactive ray detecting therapeutic apparatus according to claim 1 or 2 wherein said radioactive ray detecting means is a scintillator.

29. A radioactive ray detecting therapeutic apparatus according to claim 1 or 2 wherein said radioactive ray detecting means is a scintillating plastic optical fiber.

* * * * *